(12) United States Patent
Wityak et al.

(10) Patent No.: US 8,691,824 B2
(45) Date of Patent: Apr. 8, 2014

(54) CERTAIN KYNURENINE-3-MONOOXYGENASE INHIBITORS, PHARMACEUTICAL COMPOSITIONS, AND METHODS OF USE THEREOF

(75) Inventors: John Wityak, Carlsbad, CA (US); Leticia M. Toledo-Sherman, Santa Monica, CA (US); Celia Dominguez, Los Angeles, CA (US); Stephen Martin Courtney, Oxfordshire (GB); Christopher John Yarnold, Oxfordshire (GB); Paula C. De Aguiar Pena, Oxfordshire (GB); Andreas Scheel, Halstenbek (DE); Dirk Winkler, Hamburg (DE)

(73) Assignee: CHDI Foundation, Inc., New York, NY (US)

( * ) Notice: Subject to any disclaimer, the term of this patent is extended or adjusted under 35 U.S.C. 154(b) by 148 days.

(21) Appl. No.: 13/056,919

(22) PCT Filed: Aug. 3, 2009

(86) PCT No.: PCT/US2009/052560
§ 371 (c)(1),
(2), (4) Date: Jun. 8, 2011

(87) PCT Pub. No.: WO2010/017132
PCT Pub. Date: Feb. 11, 2010

(65) Prior Publication Data
US 2012/0329812 A1  Dec. 27, 2012

Related U.S. Application Data

(60) Provisional application No. 61/086,083, filed on Aug. 4, 2008.

(51) Int. Cl.
*A61K 31/497* (2006.01)

(52) U.S. Cl.
USPC .............. 514/254.04; 514/254.01; 544/367

(58) Field of Classification Search
USPC ............................................ 514/254.04, 256
See application file for complete search history.

(56) References Cited

U.S. PATENT DOCUMENTS

| | | | |
|---|---|---|---|
| 7,022,725 B2 | 4/2006 | Momose et al. | |
| 7,994,338 B2 * | 8/2011 | Muchowski et al. | 548/197 |
| 8,071,631 B2 * | 12/2011 | Muchowski et al. | 514/361 |
| 2004/0204464 A1 | 10/2004 | Al-Abed | |
| 2008/0070937 A1 * | 3/2008 | Muchowski et al. | 514/275 |
| 2008/0113997 A1 | 5/2008 | Sielecki-Dzurdz et al. | |
| 2011/0183957 A1 * | 7/2011 | Wityak et al. | 514/210.2 |

OTHER PUBLICATIONS

International Search Report and Written Opinion for PCT/US2009/052560, mailed Sep. 29, 2009, 8 pages.

* cited by examiner

*Primary Examiner* — My-Chau T Tran

(57) ABSTRACT

Certain chemical entities are provided herein. Also provided are pharmaceutical compositions comprising at least one chemical entity and one or more pharmaceutically acceptable vehicle. Methods of treating patients suffering from certain diseases and disorders responsive to the inhibition of KMO activity are described, which comprise administering to such patients an amount of at least one chemical entity effective to reduce signs or symptoms of the disease or disorder are disclosed. These diseases include neurodegenerative disorders such as Huntington's disease. Also described are methods of treatment include administering at least one chemical entity as a single active agent or administering at least one chemical entity in combination with one or more other therapeutic agents. Also provided are methods for screening compounds capable of inhibiting KMO activity.

20 Claims, No Drawings

CERTAIN KYNURENINE-3-MONOOXYGENASE INHIBITORS, PHARMACEUTICAL COMPOSITIONS, AND METHODS OF USE THEREOF

This application is a National Stage application of PCT Application No. PCT/US2009/52560, filed Aug. 3, 2009, which claims priority to U.S. Provisional Application No. 61/086,083, filed Aug. 4, 2008, which is incorporated herein by reference.

Provided herein are certain kynurenine-3-monooxygenase inhibitors, pharmaceutical compositions thereof, and methods of their use.

Kynurenine-3-monooxygenase (KMO) is an enzyme in the tryptophan degradation pathway that catalyzes the conversion of kynurenine into 3-hydroxykynurenine (3-HK), which is a precursor of the neurotoxin quinolinic acid (QUIN). Therefore, compounds which act as inhibitors of KMO are of particular interest since they may block the metabolism toward QUIN and at the same time, may increase the formation of neuroprotective metabolite kynurenic acid (KYNA).

KMO inhibitors have been proposed as therapeutic agents for the treatment of neurodegenerative disease such Huntington's disease, Alzheimer's disease, dementia caused by Acquired Immunodeficiency Syndrome (AIDS), infarctual dementia, cerebral ischemia, cerebral hypoxia, Parkinson's disease, epilepsy, head and spinal cord injury, amyotrophic lateral sclerosis, glaucoma retinopathy, infections of the brain or inflammations of the brain. There remains a need for compounds that are effective inhibitors of KMO and may be used in treating neurodegenerative disorders.

Provided is at least one chemical entity chosen from compounds of formula I

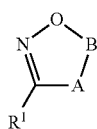

Formula I and pharmaceutically acceptable salts and prodrugs thereof wherein:

$R^1$ is chosen from aryl and heteroaryl, each of which is substituted with one, two, or three groups chosen from halo, lower alkyl, lower alkoxy, optionally substituted amino, optionally substituted heterocycloalkyl, optionally substituted heteroaryl, and hydroxy;

A-B is chosen from —$CH_2$—$C(R^2)H$—, —$CH$=$C(R^2)$—, —$C(R^2)H$—$C(R^9)H$—, and —$C(R^2)$=$CH_2$—;

$R^2$ is —$(CR^3R^4)_n$—X—$R^5$;

$R^3$ and $R^4$ are independently chosen from hydrogen and lower alkyl;

$R^5$ is chosen from hydrogen, optionally substituted alkyl, optionally substituted cycloalkyl, optionally substituted heterocycloalkyl, optionally substituted aryl, and optionally substituted heteroaryl;

n is chosen from 1 and 2;

X is chosen from —C(O)—, —C(=$NR^6$)—, —SO—, —$SO_2$—, —C(O)O—, —$NR^7$C(O)—, —C(O)$NR^7$—, —$NR^7$C(S)—, —C(S)$NR^7$—, —$NR^7$C(O)O—, —OC(O)$NR^7$—, —$SO_2$—$NR^7$—, —$NR^7SO_2$—, —$NR^7$C(O)$NR^7$—, —$NR^7$C(S)$NR^7$—, —C(=$NR^6$)$NR^7$—, —$NR^7$C(=$NR^7$)$NR^7$—, —$NR^7$—$SO_2NR^7$— and —O—$SO_2NR^7$—;

$R^6$ is —$OR^8$ where $R^8$ is chosen from hydrogen, optionally substituted lower alkyl, optionally substituted cycloalkyl, optionally substituted aryl, optionally substituted heterocycloalkyl, and optionally substituted heteroaryl;

$R^7$ is chosen from hydrogen, optionally substituted lower alkyl, optionally substituted cycloalkyl, optionally substituted aryl, optionally substituted heterocycloalkyl, and optionally substituted heteroaryl, or $R^5$ taken together with $R^7$, and any intervening atoms, forms an optionally substituted heterocycloalkyl or optionally substituted heteroaryl ring;

$R^9$ is chosen from hydrogen and lower alkyl;

provided that the compound of Formula I is not tert-butyl 2-(3-(3-fluoro-4-hydroxyphenyl)-4,5-dihydroisoxazol-5-yl)acetate, provided that if A-B is —$CH_2$—$C(R^2)H$— and n is 1, then $R^1$ is not 4-hydroxyphenyl, 2-hydroxyphenyl, or 2,4-dihydroxyphenyl;

provided that if A-B is —$CH_2$—$C(R^2)H$—, n is 2, and X is —C(O)O—, then $R^1$ is not 4-hydroxyphenyl;

provided that if A-B is —$CH_2$—$C(R^2)H$—, n is 2, X is —C(O)— and $R^5$ is hydrogen, then $R^1$ is not 3,4-dimethoxyphenyl, phenyl, 3-phenoxyphenyl, 4-fluorophenyl, 3-nitrophenyl, or 2-thienyl;

provided that if A-B is —$CH_2$—$C(R^2)H$—, n is 1, and X is —C(O)O—, then $R^1$ is not 3,5-di-tert-butyl-4-hydroxyphenyl or 3-fluoro-4-hydroxyphenyl;

provided that if A-B is —$CH_2$—$C(R^2)H$—, n is 1, and X is —C(S)—$NR^7$, then $R^1$ is not 4-bromophenyl; and provided that if A-B is —$CH_2$—$C(R^2)H$—, n is 1, and X is —C(O)—$NR^7$, then $R^1$ is not 4-chlorophenyl, 2,4-difluorophenyl, 3,4-difluorophenyl, 2-fluoro-4-hydroxyphenyl, 3,5-di-tert-butyl-4-hydroxyphenyl, 4-bromophenyl, or 2,4-difluoro-6-methoxyphenyl.

Also provided is a pharmaceutical composition comprising at least one chemical entity described herein and at least one pharmaceutically acceptable excipient.

Also provided is a packaged pharmaceutical composition comprising at least one pharmaceutical composition described herein and instructions for using the composition to treat a subject suffering from a condition or disorder mediated by Kynurenine 3-mono-oxygenase activity.

Also provided is a method of treating a condition or disorder mediated by Kynurenine 3-mono-oxygenase activity in a subject in need of such a treatment which method comprises administering to the subject a therapeutically effective amount of at least one chemical entity described herein.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O) (optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —$S(O_2)$-(optionally substituted ($C_1$-$C_6$)alkyl), —$S(O_2)$-optionally substituted aryl), —$S(O_2)$-optionally substituted heteroaryl), —$S(O_2)$-(optionally substituted heterocycloalkyl), —$S(O_2)$-(optionally substituted alkoxy), —$S(O_2)$-optionally substituted aryloxy), —$S(O_2)$-optionally substituted heteroaryloxy), —$S(O_2)$-(optionally substituted heterocyclyloxy); and —$S(O_2)$-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

"Aryl" encompasses:
  5- and 6-membered carbocyclic aromatic rings, for example, benzene;
  bicyclic ring systems wherein at least one ring is carbocyclic and aromatic, for example, naphthalene, indane, and tetralin; and
  tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
  5- to 7-membered aromatic, monocyclic rings containing one or more, for example, from 1 to 4, or In some embodiments, from 1 to 3, heteroatoms chosen from N, O, and S, with the remaining ring atoms being carbon; and
  bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For example, heteroaryl also includes a 5- or 6-membered heterocycloalkyl, aromatic ring fused to a 5- to 7-membered aryl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide ($-O^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolidinyl, 2,4-imidazolidinyl, 2,3-pyrazolidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholinyl, piperazinyl, and piperidinyl), and heteroaryl (including without limitation pyridinyl and pyrimidinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1\text{-}C_2$ alkyl)$O$— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$—$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derviatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-performance liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Chemical entities include, but are not limited to compounds described herein and all pharmaceutically acceptable forms thereof. Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs. Hence, the terms "chemical entity" and "chemical entities" also encompass pharmaceutically acceptable salts, prodrugs, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities described herein. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_5-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromitic carbon that bears a hydrogen-.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-neurodegenerative therapeutic.

The term "therapeutically effective amount" of a chemical entity described herein means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity. In some embodiments, a therapeutically effective amount is an amount sufficient to treat the symptoms of neurodegenerative pathway or disease, such as Huntington's disease, Alzheimer's disease, Parkinson's disease, olivoponto cerebellar atrophy, non-Alzheimer's dementia, multi-infarctual dementia, cerebral amyotrophic lateral sclerosis, cerebral ischemia, cerebral hypoxia, spinal or head trauma, or epilepsy. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of neuronal cell death. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of QUIN associated with neuronal cell death. In some embodiments, a therapeutically effective amount of a chemical entity is an amount sufficient to effect an increase in the level of KYNA associated with neuronal cell health. In some embodiments, a therapeutically effective amount of a chemical entity is an amount sufficient to increase the anticonvulsant and neuroprotective properties associated with lowered levels of QUIN and increased levels of KYNA.

In methods described herein for treating a neurodegenerative disorder, a therapeutically effective amount may also be an amount sufficient, when administered to a patient, to detectably slow the progression of the neurodegenerative disease, or prevent the patient to whom the chemical entity is given from presenting symptoms of the neurodegenerative disease. In some methods described herein for treating a neurodegenative disease, a therapeutically effective amount may also be an amount sufficient to produce a detectable decrease in the level of neuronal cell death. For example, in some embodiments a therapeutically effective amount is an amount of a chemical entity described herein sufficient to significantly decrease the level of neuronal death by effecting a detectable decrease in the amount of QUIN, and an increase in the amount of KYNA.

The term "inhibition" indicates a significant decrease in the baseline activity of a biological activity or process. "Inhibition of KMO activity" refers to a decrease in KMO activity as a direct or indirect response to the presence of at least one chemical entity described herein, relative to the activity of KMO in the absence of at least one chemical entity. The decrease in activity may be due to the direct interaction of the compound with KMO, or due to the interaction of the chemical entity(ies) described herein with one or more other factors that in turn affect KMO activity. For example, the presence of the chemical entity(ies) may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one chemical entity described herein, relative to the activity of KMO in the absence of the at least one chemical entity. The decrease in activity may be due to the direct interaction of the compound with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the chemical entity described herein has an $IC_{50}$ value less than or equal to 1 micromolar. In some embodiments, the chemical entity has an $IC_{50}$ value less than or equal to less than 100 micromolar. In some embodiments, the chemical entity has an $IC_{50}$ value less than or equal to 10 nanomolar.

"KMO activity" also includes activation, redistribution, reorganization, or capping of one or more various KMO membrane receptors, or receptor sites can undergo redistribution and capping that can initiate signal transduction. KMO activity also includes the synthesis or production of QUIN and 3-HK.

A "disease responsive to inhibition of KMO activity" is a disease in which inhibiting KMO provides a therapeutic benefit such as an amelioration of symptoms, decrease in disease progression, prevention or delay of disease onset, or inhibition of aberrant activity and/or death of certain cell-types (neuronal cells).

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is at least one chemical entity chosen from compounds of formula I

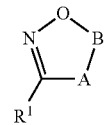

Formula I and pharmaceutically acceptable salts and prodrugs thereof wherein:

$R^1$ is chosen from aryl and heteroaryl, each of which is substituted with one, two, or three groups chosen from halo, lower alkyl, lower alkoxy, optionally substituted amino, optionally substituted heterocycloalkyl, optionally substituted heteroaryl, and hydroxy;

A-B is chosen from —$CH_2$—$C(R^2)H$—, —$CH$=$C(R^2)$—, —$C(R^2)H$—$C(R^9)H$—, and —$C(R^2)$=$CH_2$—;

$R^2$ is —$(CR^3R^4)_n$—X—$R^5$;

$R^3$ and $R^4$ are independently chosen from hydrogen and lower alkyl;

$R^5$ is chosen from hydrogen, optionally substituted alkyl, optionally substituted cycloalkyl, optionally substituted heterocycloalkyl, optionally substituted aryl, and optionally substituted heteroaryl;

n is chosen from 1 and 2;

X is chosen from —C(O)—, —C(=$NR^6$)—, —SO—, —$SO_2$—, —C(O)O—, —$NR^7C(O)$—, —C(O)$NR^7$—, —$NR^7C(S)$—, —C(S)$NR^7$—, —$NR^7C(O)O$—, —OC(O)$NR^7$—, —$SO_2$—$NR^7$—, —$NR^7SO_2$—, —$NR^7C(O)$ —NR⁷—, —NR⁷C(S)NR⁷—, —C(=NR⁶)NR⁷—, —NR⁷C(=NR⁷)NR⁷—, —NR⁷—SO₂NR⁷— and —O—SO₂NR⁷—;

R⁶ is —OR⁸ where R⁸ is chosen from hydrogen, optionally substituted lower alkyl, optionally substituted cycloalkyl, optionally substituted aryl, optionally substituted heterocycloalkyl, and optionally substituted heteroaryl;

R⁷ is chosen from hydrogen, optionally substituted lower alkyl, optionally substituted cycloalkyl, optionally substituted aryl, optionally substituted heterocycloalkyl, and optionally substituted heteroaryl, or R⁵ taken together with R⁷, and any intervening atoms, forms an optionally substituted heterocycloalkyl or optionally substituted heteroaryl ring;

R⁹ is chosen from hydrogen and lower alkyl;

provided that the compound of Formula I is not tert-butyl 2-(3-(3-fluoro-4-hydroxyphenyl)-4,5-dihydroisoxazol-5-yl)acetate, provided that if A-B is —CH₂—C(R²)H— and n is 1, then R¹ is not 4-hydroxyphenyl, 2-hydroxyphenyl, or 2,4-dihydroxyphenyl;

provided that if A-B is —CH₂—C(R²)H—, n is 2, and X is —C(O)O—, then R¹ is not 4-hydroxyphenyl;

provided that if A-B is —CH₂—C(R²)H—, n is 2, X is —C(O)— and R⁵ is hydrogen, then R¹ is not 3,4-dimethoxyphenyl, phenyl, 3-phenoxyphenyl, 4-fluorophenyl, 3-nitrophenyl, or 2-thienyl;

provided that if A-B is —CH₂—C(R²)H—, n is 1, and X is —C(O)O—, then R¹ is not 3,5-di-tert-butyl-4-hydroxyphenyl or 3-fluoro-4-hydroxyphenyl;

provided that if A-B is —CH₂—C(R²)H—, n is 1, and X is —C(S)—NR⁷, then R¹ is not 4-bromophenyl; and provided that if A-B is —CH₂—C(R²)H—, n is 1, and X is —C(O)—NR⁷, then R¹ is not 4-chlorophenyl, 2,4-difluorophenyl, 3,4-difluorophenyl, 2-fluoro-4-hydroxyphenyl, di-tert-butyl-4-hydroxyphenyl, 4-bromophenyl, or 2,4-difluoro-6-methoxyphenyl.

Provided is at least one chemical entity chosen from compounds of formula I

Formula I and pharmaceutically acceptable salts and prodrugs thereof wherein:

R¹ is chosen from aryl and heteroaryl, each of which is substituted with one, two, or three groups chosen from halo, lower alkyl, lower alkoxy, optionally substituted amino, optionally substituted heterocycloalkyl, optionally substituted heteroaryl, and hydroxy;

A-B is chosen from —CH₂—C(R²)H—, —CH=C(R²)—, —C(R²)H—CH₂—, and —C(R²)=CH₂—;

R² is —(CR³R⁴)ₙ—X—R⁵;

R³ and R⁴ are independently chosen from hydrogen and lower alkyl;

R⁵ is chosen from hydrogen, optionally substituted alkyl, optionally substituted cycloalkyl, optionally substituted heterocycloalkyl, optionally substituted aryl, and optionally substituted heteroaryl;

n is chosen from 1 and 2;

X is chosen from —C(O)—, —C(=NR⁶), —SO—, —SO₂—, —C(O)O—, —NR⁷C(O)—, —C(O)NR⁷—, —NR⁷C(S)—, —C(S)NR⁷—, —NR⁷C(O)O—, —OC(O)NR⁷—, —SO₂—NR⁷—, —NR⁷SO₂—, NR⁷C(O)NR⁷—, —NR⁷C(S)NR⁷—, —C(=NR⁶)NR⁷—, —NR⁷C(=NR⁷)NR⁷—, —NR⁷—SO₂NR⁷— and —O—SO₂NR⁷—, R⁶ is —OR⁸ where R⁸ is chosen from hydrogen, optionally substituted lower alkyl, optionally substituted cycloalkyl, optionally substituted aryl, optionally substituted heterocycloalkyl, and optionally substituted heteroaryl;

R⁷ is chosen from hydrogen, optionally substituted lower alkyl, optionally substituted cycloalkyl, optionally substituted aryl, optionally substituted heterocycloalkyl, and optionally substituted heteroaryl, or R⁵ taken together with R⁷, and any intervening atoms, forms an optionally substituted heterocycloalkyl or optionally substituted heteroaryl ring;

provided that the compound of Formula I is not tert-butyl 2-(3-(3-fluoro-4-hydroxyphenyl)-4,5-dihydroisoxazol-5-yl)acetate, provided that if A-B is —CH₂—C(R²)H— and n is 1, then R¹ is not 4-hydroxyphenyl, 2-hydroxyphenyl, or 2,4-dihydroxyphenyl;

provided that if A-B is —CH₂—C(R²)H—, n is 2, and X is —C(O)O—, then R¹ is not 4-hydroxyphenyl;

provided that if A-B is —CH₂—C(R²)H—, n is 2, X is —C(O)— and R⁵ is hydrogen, then R¹ is not 3,4-dimethoxyphenyl, phenyl, 3-phenoxyphenyl, 4-fluorophenyl, 3-nitrophenyl, or 2-thienyl;

provided that if A-B is —CH₂—C(R²)H—, n is 1, and X is —C(O)O—, then R¹ is not 3,5-di-tert-butyl-4-hydroxyphenyl or 3-fluoro-4-hydroxyphenyl;

provided that if A-B is —CH₂—C(R²)H—, n is 1, and X is —C(S)—NR⁷, then R¹ is not 4-bromophenyl; and provided that if A-B is —CH₂—C(R²)H—, n is 1, and X is —C(O)—NR⁷, then R¹ is not 4-chlorophenyl, 2,4-difluorophenyl, 3,4-difluorophenyl, 2-fluoro-4-hydroxyphenyl, 3,5-di-tert-butyl-4-hydroxyphenyl, 4-bromophenyl, or 2,4-difluoro-6-methoxyphenyl.

In some embodiments, R¹ is chosen from optionally substituted phenyl and optionally substituted heteroaryl. In some embodiments, R¹ is chosen from pyridinyl and phenyl optionally substituted with one, two or three halo groups. In some embodiments, R¹ is phenyl optionally substituted with one or two halo groups. In some embodiments, R¹ is 3,4-dihalophenyl. In some embodiments, R¹ is 3,4-dichlorophenyl. In some embodiments, R¹ is 3-halophenyl. In some embodiments, R¹ is 3-chlorophenyl.

In some embodiments, n is one.

In some embodiments, n is two.

In some embodiments, for each occurrence, at least one of R² and R³ is hydrogen. In some embodiments, R² and R³ are hydrogen. In some embodiments, for each occurrence R² and R³ are independently lower alkyl.

In some embodiments, X is —C(O)O—. In some embodiments, R⁵ is chosen from hydrogen and lower alkyl. In some embodiments, R⁵ is chosen from hydrogen, methyl, and ethyl. In some embodiments, R⁵ is hydrogen. In some embodiments, R⁵ is lower alkyl, such as methyl or ethyl.

In some embodiments, X is chosen from —NR⁷SO₂—, —NR⁷C(O)—, and —C(O)NR⁷—. In some embodiments, X is —C(O)NR⁷—. In some embodiments, R⁷ is chosen from hydrogen and lower alkyl. In some embodiments, R⁷ is hydrogen. In some embodiments, R⁷ is methyl.

In some embodiments, X is —C(O)—. In some embodiments, X is —C(O)— and R⁵ is chosen from optionally substituted heterocycloalkyl and optionally substituted heteroaryl.

In some embodiments, $R^5$ is chosen from optionally substituted lower alkyl, optionally substituted cycloalkyl, optionally substituted aryl, optionally substituted heterocycloalkyl, and optionally substituted heteroaryl. In some embodiments, $R^5$ is chosen from optionally substituted thiadiazolyl, optionally substituted diazolyl, optionally substituted pyridinyl, optionally substituted pyrimidinyl, optionally substituted tetrazolyl, and optionally substituted oxazolyl. In some embodiments, $R^5$ is chosen from optionally substituted pyridinyl and optionally substituted pyrimidinyl. In some embodiments, $R^5$ is chosen from optionally substituted pyridin-3-yl and optionally substituted pyrimidin-5-yl. In some embodiments, $R^5$ is chosen from pyridinyl and pyrimidinyl, each of which is optionally substituted with one or two lower alkyl groups. In some embodiments, $R^5$ is chosen from pyridin-3-yl and pyrimidin-5-yl, each of which is optionally substituted with one or two lower alkyl groups.

In some embodiments, X is —C(O)NR$^7$— and $R^5$ and $R^7$, together with the nitrogen to which they are bound, form an optionally substituted heterocycloalkyl ring. In some embodiments, $R^5$ and $R^7$, together with the nitrogen to which they are bound, form an optionally substituted morpholinyl, optionally substituted piperazinyl, or optionally substituted piperidinyl ring.

In some embodiments, $R^9$ is chosen from hydrogen, methyl, ethyl, and propyl. In some embodiments, $R^9$ is hydrogen.

Also provided is at least one chemical entity chosen from compounds of Formula II

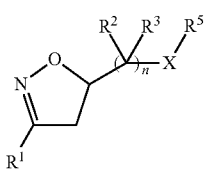

Formula II and pharmaceutically acceptable salts and prodrugs thereof wherein $R^1$, $R^2$, $R^3$, $R^5$, X, and n are as described for compounds of Formula I.

Also provided is at least one chemical entity chosen from compounds of Formula III

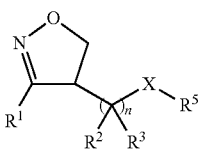

Formula III and pharmaceutically acceptable salts and prodrugs thereof wherein $R^1$, $R^2$, $R^3$, $R^5$, X, and n are as described for compounds of Formula I.

Also provided is at least one chemical entity chosen from compounds of Formula IV

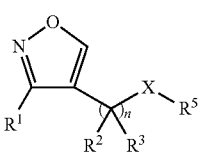

Formula IV and pharmaceutically acceptable salts and prodrugs thereof wherein $R^2$, $R^3$, $R^5$, X, and n are as described for compounds of Formula I.

Also provided is at least one chemical entity chosen from compounds of Formula V

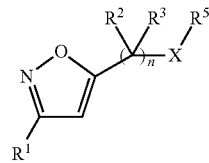

and pharmaceutically acceptable salts and prodrugs thereof wherein $R^1$, $R^2$, $R^3$, $R^5$, X, and n are as described for compounds of Formula I.

Also provided is at least one chemical entity chosen from compounds of Formula VI

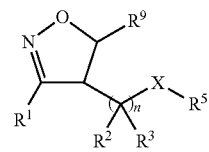

and pharmaceutically acceptable salts and prodrugs thereof wherein $R^1$, $R^2$, $R^3$, $R^5$, $R^9$, X, and n are as described for compounds of Formula I.

Also provided is at least one chemical entity chosen from
[3-(3,4-Dichloro-phenyl)-4,5-dihydro-isoxazol-4-yl]-acetic acid;
3-(3-Chloro-phenyl)-4,5-dihydro-isoxazol-4-yl]-acetic acid;
[3-(3,4-Dichloro-phenyl)-4,5-dihydro-isoxazol-5-yl]-acetic acid;
[3-(3,4-Dichloro-phenyl)-4,5-dihydro-isoxazol-5-yl]acetic acid methyl ester;
2-[3-(3,4-Dichloro-phenyl)-4,5-dihydro-isoxazol-4-yl]-N-pyridin-3-yl-acetamide;
2-[3-(3,4-Dichloro-phenyl)-4,5-dihydro-isoxazol-4-yl]-N-(2,6-dimethyl-pyridin-3-yl)-acetamide;
2-[3-(3,4-Dichloro-phenyl)-4,5-dihydro-isoxazol-4-yl]-N-(2-methyl-pyrimidin-5-yl)-acetamide;
2-[3-(3,4-Dichloro-phenyl)-4,5-dihydro-isoxazol-4-yl]-N-pyrimidin-5-yl-acetamide;
[3-(3,4-Dichloro-phenyl)-isoxazol-5-yl]acetic acid ethyl ester;
[3-(3,4-Dichloro-phenyl)-isoxazol-5-yl]-acetic acid;
[3-(3,4-Dichloro-phenyl)-isoxazol-5-yl]-acetic acid methyl ester;
[3-(3,4-Dichloro-phenyl)-isoxazol-4-yl]acetic acid;
Pyridine-3-sulfonic acid [3-(3,4-dichloro-phenyl)-4,5-dihydro-isoxazol-4-ylmethyl]-amide;
N-[3-(3,4-Dichloro-phenyl)-4,5-dihydro-isoxazol-4-ylmethyl]-nicotinamide;
2-[3-(3,4-Dichloro-phenyl)-4,5-dihydro-isoxazol-4-yl]-acetamide;
[3-(3,4-Dichloro-phenyl)-5-methyl-4,5-dihydro-isoxazol-4-yl]-acetic acid;
2-[3-(3,4-Dichloro-phenyl)-5-methyl-4,5-dihydro-isoxazol-4-yl]-N-pyrimidin-5-yl-acetamide;
2-[3-(3,4-Dichloro-phenyl)-4,5-dihydro-isoxazol-5-yl]-2-methyl-propionic acid ethyl ester;

2-[3-(3,4-Dichloro-phenyl)-4,5-dihydro-isoxazol-4-yl]-N-p-tolyl-acetamide;
2-[3-(3,4-Dichloro-phenyl)-4,5-dihydro-isoxazol-4-yl]-N-(6-methyl-pyridin-3-yl)-acetamide;
2-[3-(3,4-Dichloro-phenyl)-4,5-dihydro-isoxazol-4-yl]-1-(2,3-dihydro-pyrrolo[3,2-c]pyridin-1-yl)-ethanone;
2-[3-(3,4-Dichloro-phenyl)-4,5-dihydro-isoxazol-4-yl]-1-(2,3-dihydro-indol-1-yl)-ethanone; and
2-[3-(3,4-Dichloro-phenyl)-4,5-dihydro-isoxazol-4-yl]-N-(3-methyl-isoxazol-5-yl)-acetamide
and pharmaceutically acceptable salts and prodrugs thereof.

Also provided is at least one chemical entity chosen from
[3-(3,4-Dichloro-phenyl)-4,5-dihydro-isoxazol-4-yl]-acetic acid methyl ester;
[3-(3,4-Dichloro-phenyl)-4,5-dihydro-isoxazol-4-yl]-acetic acid;
3-(3-Chloro-phenyl)-4,5-dihydro-isoxazol-4-yl]-acetic acid;
[3-(3,4-Dichloro-phenyl)-4,5-dihydro-isoxazol-5-yl]-acetic acid;
[3-(3,4-Dichloro-phenyl)-4,5-dihydro-isoxazol-5-yl]-acetic acid methyl ester;
2-[3-(3,4-Dichloro-phenyl)-4,5-dihydro-isoxazol-4-yl]-N-pyridin-3-yl-acetamide;
2-[3-(3,4-Dichloro-phenyl)-4,5-dihydro-isoxazol-4-yl]-N-(2,6-dimethyl-pyridin-3-yl)-acetamide;
2-[3-(3,4-Dichloro-phenyl)-4,5-dihydro-isoxazol-4-yl]-(2-methyl-pyrimidin-5-yl)-acetamide;
2-[3-(3,4-Dichloro-phenyl)-4,5-dihydro-isoxazol-4-yl]-N-pyrimidin-5-yl-acetamide;
[3-(3,4-Dichloro-phenyl)-isoxazol-5-yl]-acetic acid ethyl ester; and
[3-(3,4-Dichloro-phenyl)-isoxazol-5-yl]-acetic acid,
and pharmaceutically acceptable salts and prodrugs thereof.

Methods for obtaining the chemical entitites described herein will be apparent to those of ordinary skill in the art, suitable procedures being described, for example, in the reaction schemes and examples below, and in the references cited herein.

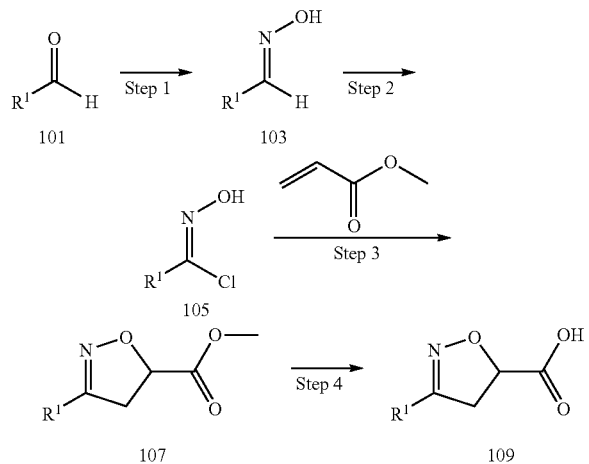

Referring to Reaction Scheme 1, Step 1, a compound of formula 101 and an excess (such as about 4 equivalents) of hydroxylamine HCl (such as about 4 equivalents) are suspended in pyridine or another suitable solvent in a sealed tube. The reaction mixture is stirred at about 50° C. overnight under an inert atmosphere. The product, a compound of formula 103, is isolated and optionally purified.

Referring to Reaction Scheme 1, Step 2, to a stirred solution of a compound of formula 103 in an inert solvent such as DMF is added an excess (such as at least about 1.1 equivalents, for example, about 1.4 equivalents) of N-chlorosuccinimide with temperature maintained between about 0-5° C. The reaction mixture is allowed to warm to room temperature. The product, a compound of formula 105 is isolated and optionally purified.

Referring to Reaction Scheme 1, Step 3, a compound of formula 105, an excess (such as about 1.1 equivalents) of methyl acrylate, and a base such as triethylamine are suspended in a suitable solvent such as THF. The reaction is stirred at room temperature overnight under an inert atmosphere. The product, a compound of formula 107, is isolated and optionally purified.

Referring to Reaction Scheme 1, Step 4, to a stirred solution of a compound of formula 107 in an inert solvent such as methanol or THF is added aqueous base, such as aqueous sodium hydroxide, for example 1M sodium hydroxide solution. The reaction mixture is stirred at room temperature. The product, a compound of formula 109, is isolated and optionally purified.

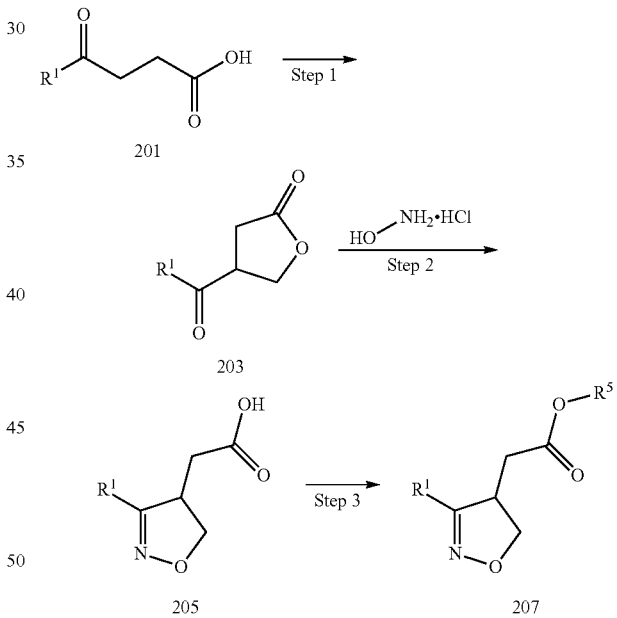

Referring to Reaction Scheme 2, Step 1, a compound of formula 201 is suspended in aqueous base such as a 0.5M NaOH solution. An excess (such as about 1.1 equivalents) of a formaldehyde solution (for example, a formaldehyde solution that is 37% by mass) is added and the reaction mixture is stirred at room temperature. The product, a compound of formula 203, is isolated and optionally purified.

Referring to Reaction Scheme 2, Step 2, a compound of formula 203 and an excess (such as about 2 equivalents) of hydroxylamine HCl and an excess (such as about 2 equivalents) of ammonium acetate are suspended in a suitable solvent (such as a mixture of an alcohol and water, for example, ethanol and water) in a sealed tube. The reaction mixture is allowed to stir at about 100° C. for about 4 hours. The product, a compound of formula 205, is isolated and optionally purified.

Referring to Reaction Scheme 2, Step 3, to a stirred solution of a compound of formula 205, in a suitable solvent such as chloroform is added about an equivalent of CDI. The reaction mixture is stirred at ambient temperature for about 30 minutes. An alcohol of formula $R^5OH$ is added and the reaction stirred at ambient temperature for about 16 hours. The product, a compound of formula 207, is isolated and optionally purified.

Reaction Scheme 3

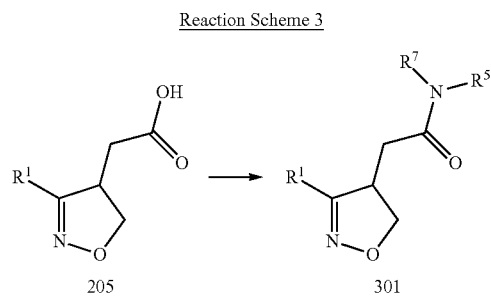

Referring to Reaction Scheme 3, to a solution of a carboxylic acid of formula 205 in an inert solvent such as DMF are added about an equivalent of EDC.HCl and about an equivalent of HOBt. The reaction mixture is stirred at ambient temperature for about 30 minutes after which time the appropriate amine of formula $NHR^5R^7$ is added. The product, a compound of formula 301, is isolated and optionally purified.

Reaction Scheme 4

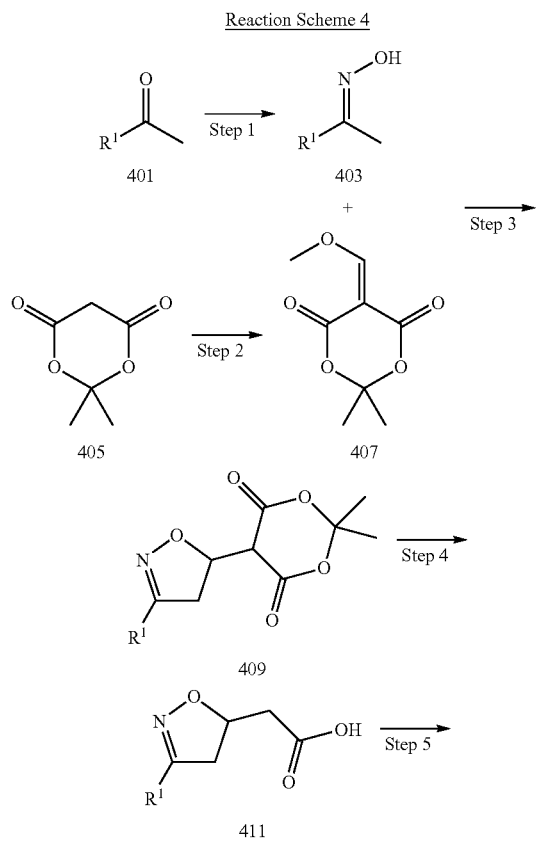

-continued

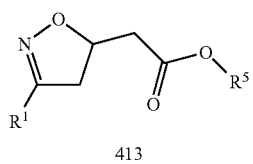

413

Referring to Reaction Scheme 4, Step 1, a mixture of a compound of formula 401, an excess (such as about 5 equivalents) of a base (such as pyridine), and an excess (such as about 5 equivalents) of hydroxylamine in a suitable solvent such as ethanol is heated to a temperature of about 90° C. for about 80 minutes. The product, a compound of formula 403, is isolated and optionally purified.

Referring to Reaction Scheme 4, Step 2, to a compound of formula 405 is added trimethylorthoformate and the mixture is heated to a temperature of about 105° C. for about 3 hours under an inert atmosphere. The product, a compound of formula 407, is isolated and optionally purified.

Referring to Reaction Scheme 4, Step 3, to a stirred solution of a compound of formula 403 in an inert solvent such as THF, cooled to about −15° C. is added an excess (such as about 2.2 equivalents) of a solution of n-butyl lithium (such as a 2.5M solution). After stirring the reaction mixture for about 75 minutes, a compound of formula 407 in an inert solvent such as THF is added. After about 1 hour the reaction mixture is warmed to about 0° C. for about 15 minutes, and then stirred for about 16 hours at room temperature. The product, a compound of formula 409, is isolated and optionally purified.

Referring to Reaction Scheme 4, Step 4, water is added to the compound of formula 409, dissolved in an inert solvent such as DMF and the mixture is heated at a temperature of about 110° C. for about 45 minutes. The product, a compound of formula 411, is isolated and optionally purified.

Referring to Reaction Scheme 4, Step 5, an excess (such as about 5 equivalents) of acetyl chloride is added to an alcohol of formula $R^5OH$ externally cooled. After about 10 minutes the solution is warmed to room temperature. After about 90 minutes, a solution of a compound of formula 411, in an alcohol of formula $R^5OH$ is added and stirred for about 16 hours. The product, a compound of formula 413, is isolated and optionally purified.

Reaction Scheme 5

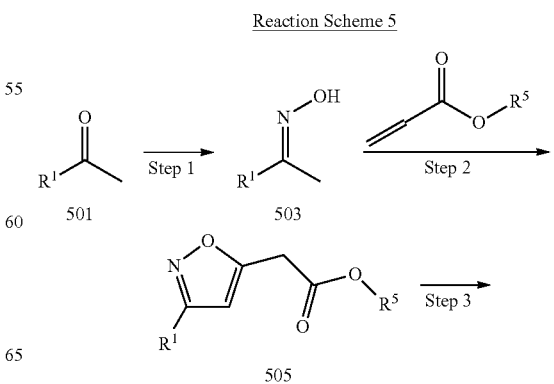

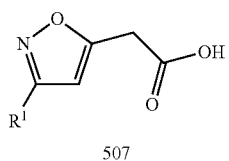

507

Referring to Reaction Scheme 5, Step 1, a mixture of a compound of formula 501, an excess (such as about 5 equivalents) of a base such as pyridine, and an excess (such as about 5 equivalents) of hydroxylamine in a suitable solvent such as EtO is heated to a temperature of about 90° C. for about 80 minutes. The product, a compound of formula 503, is isolated and optionally purified.

Referring to Reaction Scheme 5, Step 2, to a solution of ethyl 2,3-butadienoate and an excess (such as about 1.03 equivalents) of a compound of formula 503 in an inert solvent such as DCM is added 10% aqueous NaOCl (bleach) solution and the resultant biphasic system is stirred at room temperature for about 5 days. The product, a compound of formula 505, is isolated and optionally purified.

Referring to Reaction Scheme 5, Step 3, to a solution of a compound of formula 505 in an inert solvent such as in EtOH is added aqueous base (such as an aqueous solution of NaOH, for example 2M NaOH) and the mixture is stirred at room temperature. The product, a compound of formula 507, is isolated and optionally purified.

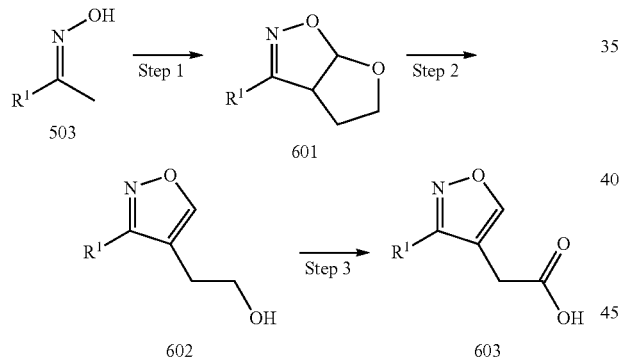

Referring to Reaction Scheme 6, Step 1, to a mixture of a compound of formula 503 in a suitable solvent, such as dichloromethane, is added an excess of a bleach solution (sodium hypochlorite) and 2,3 dihydrofuran. The mixture is stirred at room temperature for about 19 hours. The product, a compound of formula 601, is isolated and optionally purified.

Referring to Reaction Scheme 6, Step 2, to a solution of a compound of formula 601 in a suitable solvent, such as ethanol, is added concentrated acid, such as concentrated HCl. The mixture is stirred for about 27 hours and the product, a compound of formula 602, is isolated and optionally purified.

Referring to Reaction Scheme 6, Step 3, to a cooled mixture of a compound for formula 602 in an acid, such as acetic acid, is added an excess $CrO_3$ (such as about 1.3 equivalents). The mixture is allowed to warm to room temperature and stirred for about one day. Additional $CrO_3$ may be added and the mixture may be stirred for about 2 hours. The product, a compound of formula 603 is isolated and optionally purified.

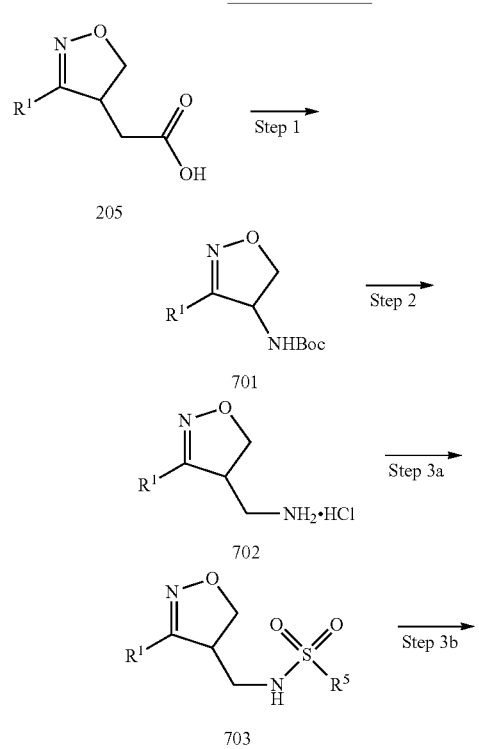

Referring to Reaction Scheme 7, Step 1, warm tert-butanol is added to a compound of formula 205 at about 30° C. Triethylamine (about 1 equivalent) is added and the mixture is stirred for about 5 minutes. A suitable coupling agent, for example DPPA (diphenyl phosphoryl azide, about 1 equivalent) is added and the mixture is stirred at about 80° C. for about 24 hours. The product, a compound of formula 701 is isolated and optionally purified.

Referring to Reaction Scheme 7, Step 2, to a compound of formula 701 is added a solution of acid, for example, HCl, in a suitable solvent, for example methanol. The mixture is stirred for about 21 hours and an additional amount of a solution of acid, for example, HCl, in a suitable solvent, for example methanol is added and the mixture is stirred for about 3.5 hours. The product, a compound of formula 702 is isolated and optionally purified.

Referring to Reaction Scheme 7, Step 3a, to a mixture of a compound of formula 702 and an excess of a compound of formula $R^5SO_2Cl$ (such as about 1.5 equivalents) is added pyridine and the mixture is stirred at room temperature for about 2 hours. The product, a compound of formula 703, is isolated and optionally purified.

Referring to Reaction Scheme 7, Step 3b, to a mixture of a compound of formula $R^5CO_2H$ (about 1.0 equivalent) in a suitable solvent, such as DMF, is added an excess of a coupling agent, such as HOBt (such as about 1.2 equivalents) and EDC.HCl (such as about 1.2 equivalents) at room temperature. To the mixture is added the free base of a compound of formula 702 and the mixture is stirred at room temperature for about 18 hours. The product, a compound of formula 704 is isolated and optionally purified.

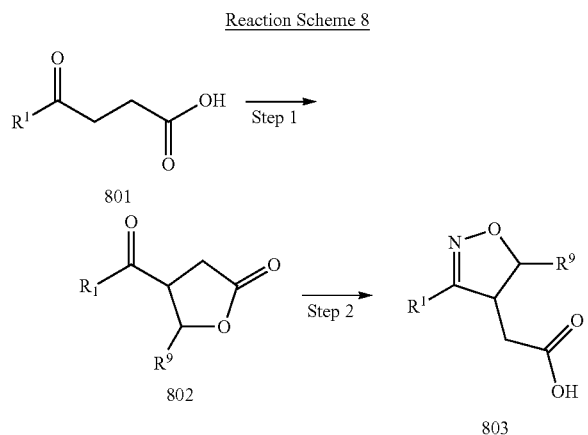

Reaction Scheme 8

Referring to Reaction Scheme 8, Step 1, to a compound of formula 801 in water is added a suitable base, such as $K_2CO_3$ (such as about 0.73 equivalent) and an aldehyde of formula $R^5$—C(O)H (such as about 1.1 equivalents) and the mixture is stirred at room temperature for about 18 hours. Concentrated acid, for example HCl, is added and the mixture is heated to about 100° C. for about 2 hours. The product, a compound of formula 802 is isolated and optionally purified.

Referring to Reaction Scheme 8, Step 2, to a compound of formula 802 in a suitable solvent, for example ethanol and water, is added an excess of hydroxylamine hydrochloride (such as about 1.48 equivalents) and ammonium acetate (such as about 1.48 equivalents). The mixture is heated to about 90° C. for about 4 hours and cooled. The product, a compound of formula 803, is isolated and optionally purified.

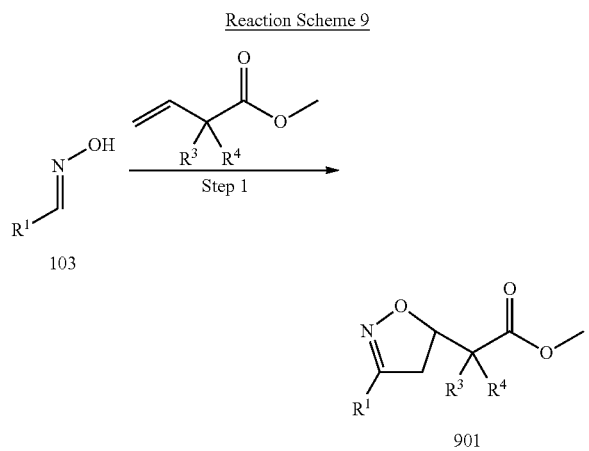

Reaction Scheme 9

Referring to Reaction Scheme 9, Step 1, to a compound of formula 103 in a suitable solvent, for example dichloromethane, is added a 10% bleach solution and an excess of an ester of formula $CH_2CHC(R^3)(R^4)C(O)OCH_3$ (such as about 3.4 equivalents). The mixture is stirred at room temperature for about 2 hours and the product, a compound of formula 901 is isolated and optionally purified.

Provided is a method of inhibiting the catalytic activity of KMO, comprising contacting said KMO with an effective amount of at least one chemical entity described herein.

Also provided is a method of treating a condition or disorder mediated by KMO activity in a subject in need of such a treatment, comprising administering to the subject a therapeutically effective amount of at least one chemical entity described herein.

Also provided is a method of treating a neurodegenerative pathology mediated by KMO activity in a subject in need of such a treatment, comprising administering to the subject a therapeutically effective amount of at least one chemical entity described herein. Also provided is a method for treating disorders mediated by (or at least in part by) the presence of KYNA and/or QUIN. Such diseases include, for example, Huntington's disease and other polyglutamine disorders such as spinocerebellar ataxias, Alzheimer's disease, Parkinson's disease, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behavior, schizophrenia, chronic anxiety, depressive disorders, disorders of the developing or aged brain, diabetes, and complications thereof, comprising administering to the subject an effective amount of at least one chemical entity described herein.

Also provided are methods of treatment in which at least one chemical entity described herein is the only active agent given to the subject and also includes methods of treatment in which at least one chemical entity described herein is given to the subject in combination with one or more additional active agents.

In general, the chemical entities described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the chemical entities described herein are administered as a pharmaceutical composition. Accordingly, provided are pharmaceutical compositions comprising at least one chemical entity described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils;

vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity described herein.

Effective concentrations of at least one chemical entity described herein are mixed with a suitable pharmaceutically acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one chemical entity described herein. In some embodiments, oral pharmaceutical compositions contain at least 5% (weight %) of at least one chemical entity described herein. Some embodiments contain from 25% to 50% or from 5% to 75% of at least one chemical entity described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

Chemical entities described herein can be incorporated into oral liquid preparations such as aqueous or oily suspensions, solutions, emulsions, syrups, or elixirs, for example. Moreover, pharmaceutical compositions containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entites described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical pharmaceutical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the chemical entity include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one chemical entity described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one chemical entity described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the chemical entities can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one chemical entity described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one chemical entity described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one chemical entity described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one chemical entity described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one chemical entity described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one chemical entity described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one chemical entity described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one chemical entity described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one chemical entity described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia comprising administering to a subject, simultaneously or sequentially, at least one chemical entity and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one chemical entity described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one chemical entity described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one chemical entity described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one chemical entity described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Also provided are packaged pharmaceutical compositions containing a pharmaceutical composition comprising at least one chemical entity described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one chemical entity described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one chemical entity described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one chemical entity described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a manner customary for KMO inhibitors. For example, the chemical entities can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one chemical entity described herein, for example, 0.1-50 mg of at least one chemical entity described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one chemical entity described herein.

A labeled form of a chemical entity described herein can be used as a diagnostic for identifying and/or obtaining compounds that have the function of modulating an activity of KMO as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The chemical entities, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc ethyl acetate
g=gram
hr=hour
hrs=hours
HOBt=N-hydroxybenotriazole
LiHMDS=lithium hexamethyl-disilazide
LC/MS=liquid chomatography/mass spectrometry
mg=milligram
min=minutes
mL=milliliter
mmol=millimoles
mM=millimolar
ng=nanogram
nm=nanometer nM=nanomolar
PBS=phosphate buffered saline
rt=room temperature
TBME=t-butyl methyl ether
THF=tetrahydrofuran
TMOF=trimethylorthoformate
μL=microliter
μM=micromolar

EXPERIMENTAL

Commercially available reagents and solvents (HPLC grade) were used without further purification.

Thin-layer chromatography (TLC) analysis was performed with Kieselgel 60 $F_{254}$ (Merck) plates and visualized using UV light. Microwave reactions were carried out using CEM focussed microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system or analytical HPLC-MS was performed on Agilent BP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software. 1 g/1 ml=1 vol General Procedures Method A: Ester Hydrolysis.

To a stirred solution of ester (1 eq) in MeOH or THF was added 1M NaOH solution. The reaction mixture was stirred at room temperature and monitored by LCMS. After completion the reaction mixture was concentrated in vacuo and the residue dissolved in water, acidified with conc HCl and extracted with DCM (3x). The combined organic layers were dried over $MgSO_4$, filtered, and the solvent removed in vacuo to give required target.

Method B: CDI Promoted Esterification.

To a stirred solution of the oxime acid (1 eq) in THF was added CDI (1 eq). The reaction mixture was stirred at ambient temperature for 30 minutes. The appropriate alcohol (1 eq) was added and the reaction stirred at ambient temperature for 16 hours. THF was removed in vacuo and the residue dissolved in $NaHCO_3$ and DCM. The organic layer was extracted with DCM (3x). The combined organic layers were washed with 1M citric acid, water, and saturated aqueous NaCl, dried over $MgSO_4$, filtered, and the solvent removed in vacuo to give crude product. Purification by flash column chromatography gave the required oxime ester.

Method C. Amide coupling.

To a solution of carboxylic acid (1 eq) in DMF were added EDC.HCl (1 eq) and HOBt (1 eq). The reaction mixture was stirred at ambient temperature for 30 minutes after which time the appropriate amine was added. The reaction was monitored by LCMS. After completion the reaction mixture was poured into water after which a precipitate came out of solution and was filtered, washed with water, heptane and dried in vacuo to yield the target compound or if a precipitate was not formed the reaction mixture was extracted with EtOAc (3x) and the combined organic layers were washed with water, saturated aqueous NaCl, dried ($Na_2SO_4$ or $MgSO_4$) and the solvent removed in vacuo to afford the crude product. Purification was carried out by flash column chromatography, prep HPLC, or a combination of both.

Method D. Amide Coupling

The carboxylic acid (1 eq), HOBt (1.4 eq) and HATU (1.3 eq) were stirred in DMF (25 vol) for 1 hour at room temperature. The relevant amine (1.5 eq) was then added and the reaction mixture stirred for 16 hours. The solvent was concentrated and the residue was triturated in a mixture of 1:1 acetonitrile and water, filtered, washed with more 1:1 acetonitrile and water, and dried.

Example 1

Preparation of 3,5-isoxazolines analogues

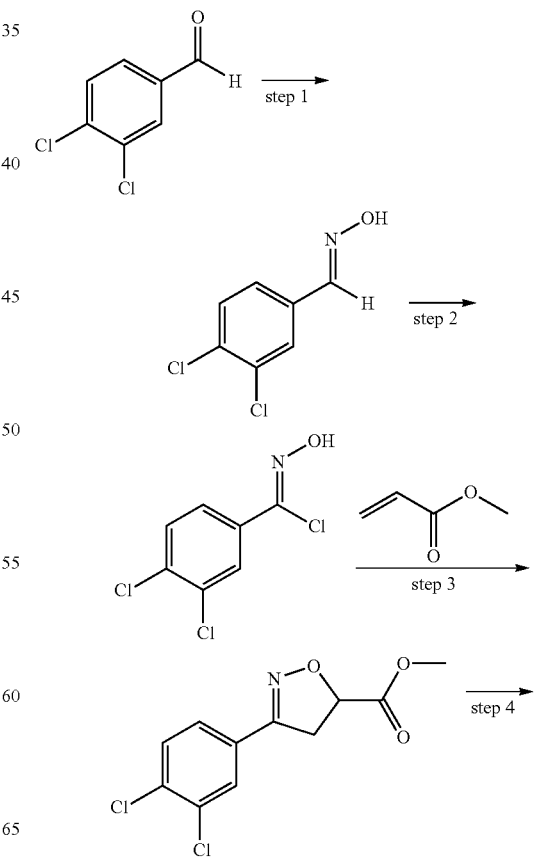

-continued

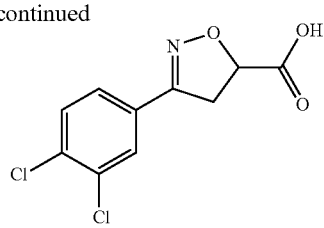

Step 1
3,4-Dichlorobenzaldehyde (1 eq) and hydroxylamine.HCl (4 eq) were suspended in pyridine (10 vol) in a sealed tube. The reaction mixture was stirred at 50° C. overnight under an atmosphere of $N_2$. The reaction mixture was concentrated in vacuo before the addition of EtOAc (10 vol) and 2M citric acid solution (5 vol). The organic layer was separated and washed with citric acid (2×5 vol) and saturated aqueous NaCl solution (5 vol). The organic layer was dried over $Na_2SO_4$, filtered and concentrated under reduced pressure to yield required 3,4-dichloro-benzaldehyde oxime.

Step 2
To a stirred solution of 3,4-dichloro-benzaldehyde oxime (1 eq) in DMF (16 vol) was added N-chlorosuccinimide (1.14 eq) with temperature maintained between 0-5° C. using an ice bath. The reaction mixture was allowed to warm to room temperature before stirring overnight under $N_2$. Upon completion, EtOAc (20 vol) was added to the reaction mixture. The organic layer was washed with a mixture of saturated aqueous NaCl solution and water (1:1) (2×20 vol), separated, dried over $Na_2SO_4$, filtered and concentrated in vacuo. The resulting residue was purified by flash column chromatography (eluent: [0:1 to 1:1] EtOAc:heptane) to afford pure target compound.

Step 3
To chloro hydroxylamine (1 eq), methyl acrylate (1.1 eq) and triethylamine (1.1 eq) were suspended in THF (20 vol). The reaction was stirred at room temperature overnight under an atmosphere of $N_2$. The reaction mixture was concentrated in vacuo before the addition of EtOAc (20 vol) and water (20 vol). The reaction mixture was extracted with EtOAc (2×20 vol). The combined organic layers were washed with saturated aqueous NaCl solution (20 vol), dried over $Na_2SO_4$, filtered and concentrated under reduced pressure. Recrystallisation from DCM yielded the required target

Step 4
The carboxylic acid analogue was prepared following the procedure described in method A (reaction was carried out in THF). The reaction mixture was acidified with 2M HCl before extracting with DCM. A precipitate was formed, filtered, washed with water (3×10 vol) and heptane (3×10 vol) before drying in vacuo to yield the target compound.

| Structure | Molecular Weight | Mass Spec Result |
|---|---|---|
| 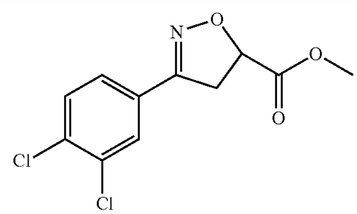 [SMILES: COC(=O)C1CC(c2ccc(Cl)c(Cl)c2)=NO1] | 274.11 | $[M + H]^+$ = 274, 100% @ rt = 4.26 min |
| 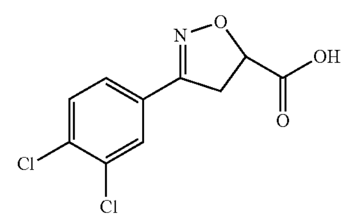 [SMILES: O=C(O)C1CC(c2ccc(Cl)c(Cl)c2)=NO1] | 260.08 | $[M + H]^+$ = 260, 100% @ rt = 3.73 min |

Example 2

Preparation of 3,4-isoxazoline analogues

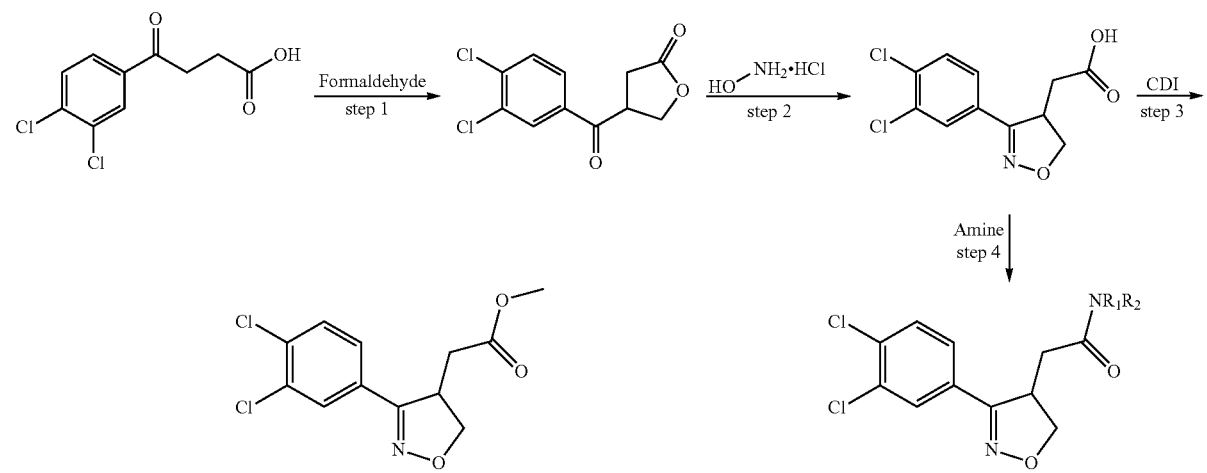

Step 1
4-(3,4-Dichloro-phenyl)-4-oxo-butyric acid (1 eq) was suspended in 0.5M NaOH solution (1.1 eq). A formaldehyde solution (37% by mass, 1.1 eq) was added and the reaction mixture and stirred at room temperature for 1 hour. HCl (conc.) was added to =pH 1. A precipitate was formed and the solution was stirred at room temperature overnight. The reaction mixture was extracted with DCM (3×10 vol). The combined organic layers were washed with saturated aqueous NaCl solution (10 vol), dried over Na$_2$SO$_4$, filtrated and concentrated in vacuo. The resulting residue was purified by flash column chromatography (eluent: [0:9 to 1:1] EtOAc:heptane) to afford pure target compound.

Step 2

4-(3,4-Dichloro-benzoyl)-dihydro-furan-2-one (1 eq), hydroxylamine.HCl (2 eq) and ammonium acetate (2 eq) were suspended in EtOH (10 vol) and water (7 vol) in a sealed tube. The reaction mixture was allowed to stir at 100° C. for 4 hours. The reaction solution was allowed to cool to room temperature before EtOH was removed in vacuo and the solution was subsequently acidified with concentrated HCl and extracted with DCM (3×20 vol). The organic layer was concentrated in vacuo and the resulting residue treated with 5% sodium bicarbonate solution (20 vol) and extracted with TBME (3×20 vol). The aqueous layer was then re-acidified with HCl to afford the required crude target as a precipitate. The precipitate was filtered and dried. Recrystallisation from EtOH yielded pure carboxylic acid.

Step 3

The required methyl ester was prepared following the procedure described in method B (reaction was carried out in CDCl$_3$). The reaction mixture was concentrated in vacuo and the crude residue was purified by flash column chromatography (eluent: [0:1 to 1:4] EtOAc:heptane) to yield required product.

Step 4

The amide analogues were prepared following the procedure described in method C. The reaction mixture was poured into water and extracted with EtOAc (3×). The combined organic layers were washed with water (vol), 1M citric acid (vol) and saturated aqueous NaCl solution (vol), dried over MgSO$_4$, filtered and concentrated in vacuo. The resultant solid required further purification and was dissolved in EtOAc (vol) and saturated aqueous NaHCO$_3$ solution (vol). The organic layer was separated and dried over MgSO$_4$, filtered and concentrated in vacuo to afford the desired product.

| Structure | Molecular Weight | Mass Spec Result |
|---|---|---|
| | 288.13 | [M + H]$^+$ = 288, 100% @ rt = 4.38 min |
| | 274.11 | [M + H]$^+$ = 274, 99% @ rt = 3.83 min |
| 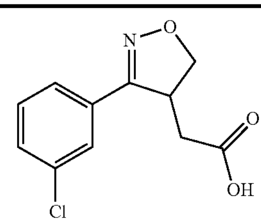 | 239.66 | [M + H]$^+$ = 240, 97% @ rt = 3.45 min |
| 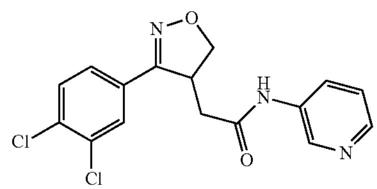 [SMILES: O=C(CC1CON=C1c1ccc(Cl)c(Cl)c1)Nc1cccnc1] | 350.21 | [M + H]$^+$ = 350, 100% @ rt = 3.21 min |
| 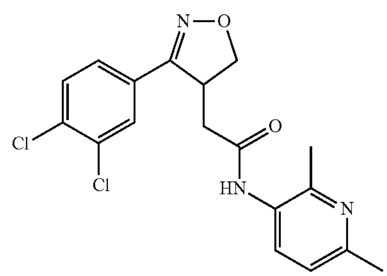 [SMILES: Cc1ccc(NC(=O)CC2CON=C2c2ccc(Cl)c(Cl)c2)c(C)n1] | 378.26 | [M + H]$^+$ = 378, 100% @ rt = 2.96 min |
| 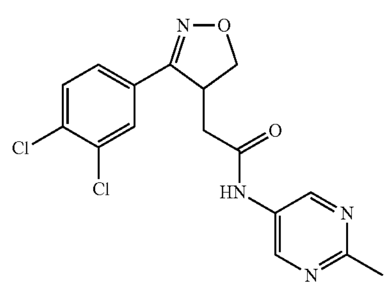 [SMILES: Cc1ncc(NC(=O)CC2CON=C2c2ccc(Cl)c(Cl)c2)cn1] | 365.22 | [M + H]$^+$ = 365, 98% @ rt = 3.72 min |
| 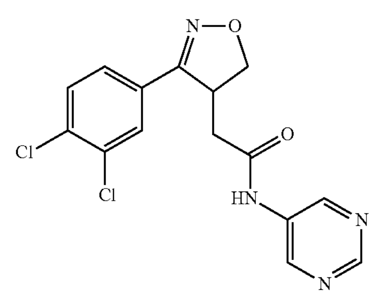 [SMILES: O=C(CC1CON=C1c1ccc(Cl)c(Cl)c1)Nc1cncnc1] | 351.19 | [M + H]$^+$ = 351, 96% @ rt = 3.67 min |

Additionally, the following amides were prepared using the procedure described in method D with the following exceptions:

For 2-[3-(3,4-Dichloro-phenyl)-4,5-dihydro-isoxazol-4-yl]-N-p-tolyl-acetamide, to the crude product was added: water, saturated NaHCO$_3$ and EtOAc. The organic phase was dried Na$_2$SO$_4$, filtered and concentrated. The residue was triturated in a mixture of 1:1 acetonitrile and water, filtered and dried to yield 2-[3-(3,4-Dichloro-phenyl)-4,5-dihydro-isoxazol-4-yl]-N-p-tolyl-acetamide For 2-[3-(3,4-Dichloro-phenyl)-4,5-dihydro-isoxazol-4-yl]-N-(6-methyl-pyridin-3-yl)-acetamide, to the crude product was added water and EtOAc. The organic phase was dried Na₂SO₄, filtered and concentrated. The crude residue was partially purified by flash column chromatography (eluent: EtOAc) and then dissolved in EtOAc and washed with saturated NaHCO₃ to remove excess HOBt, dried Na₂SO₄, filtered and concentrated to yield 2-[3-(3,4-Dichloro-phenyl)-4,5-dihydro-isoxazol-4-yl]-N-(6-methyl-pyridin-3-yl)-acetamide For 2-[3-(3,4-Dichloro-phenyl)-4,5-dihydro-isoxazol-4-yl]-N-(3-methyl-isoxazol-5-yl)-acetamide, NaH dispersion in 60% oil (2 eq) was added to the reaction. The final compound was additionally triturated with a mixture of ether and heptane to remove grease and dried to yield 2-[3-(3,4-Dichloro-phenyl)-4,5-dihydro-isoxazol-4-yl]-N-(3-methyl-isoxazol-5-yl)-acetamide

| Structure | Molecular Weight | Mass Spec. Result |
|---|---|---|
| | 363.25 | [M + H]⁺ = 363/365, 100% @ rt = 4.76 min |
| | 364.23 | [M + H]⁺ = 364/366, 100% @ rt = 3.18 min |
| 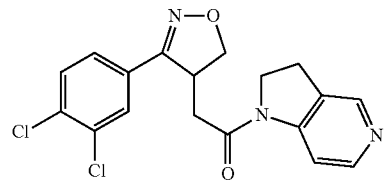 [SMILES: O=C(CC1CON=C1c1ccc(Cl)c(Cl)c1)N1CCc2cnccc21] | 376.25 | [M + H]⁺ = 376/378, 100% @ rt = 3.15 min |
| 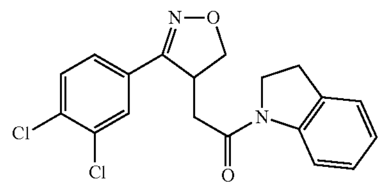 [SMILES: O=C(CC1CON=C1c1ccc(Cl)c(Cl)c1)N1CCc2ccccc21] | 375.26 | [M + H]⁺ = 375/377, 100% @ rt = 4.98 min |
| 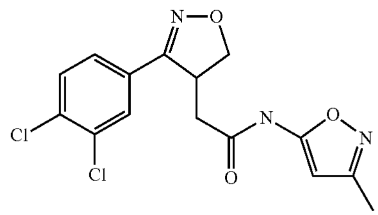 [SMILES: Cc1cc(NC(=O)CC2CON=C2c2ccc(Cl)c(Cl)c2)on1] | 354.2 | [M + H]⁺ = 354/356, 98% @ rt = 4.31 min |

Example 3

Preparation of Extended Chain 3,5-isoxazolines

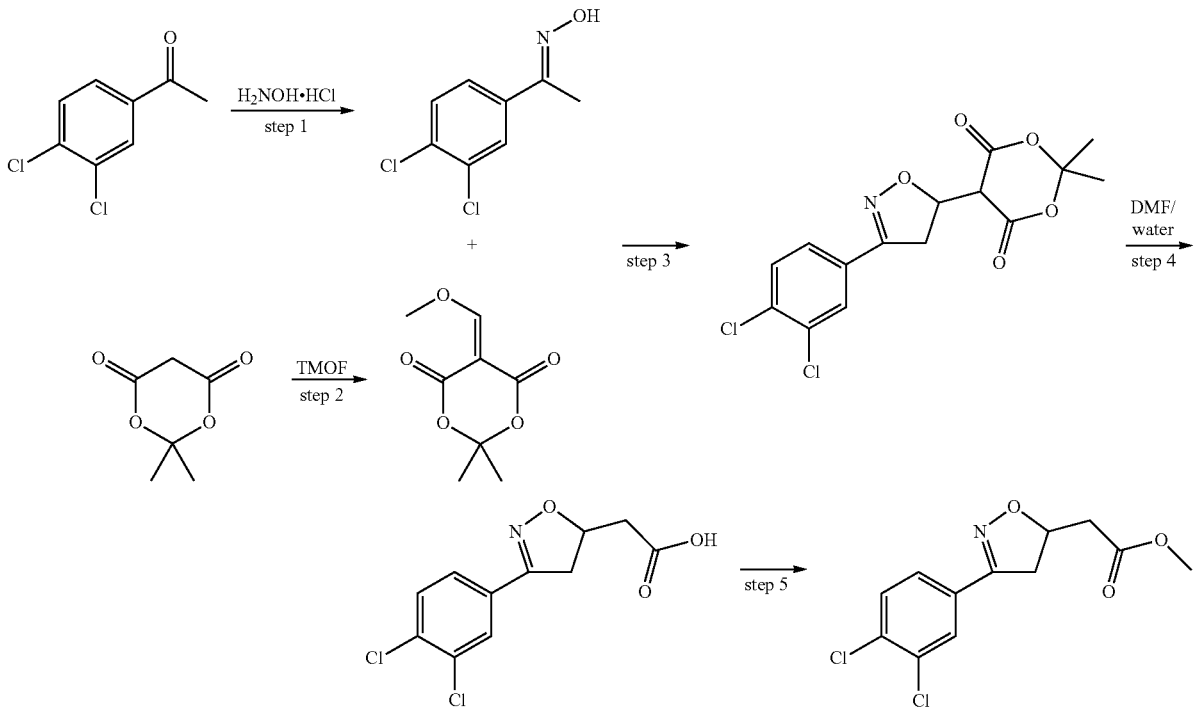

Step 1

A mixture of 3,4-dichloroacetophenone (1.0 eq), pyridine (5.0 eq) and hydroxylamine (5.0 eq) in EtOH (10 vol) was heated to a temperature of 90° C. for 80 minutes. To the cooled reaction mixture was added water (40 vol) and the precipitated solid was filtered, washed with water (2×10 vol) and dried to give 1-(3,4-dichloro-phenyl)-ethanone oxime.

Step 2

To 2,2-dimethyl-1,3-dioxane-4,6-dioxane (1.0 eq) was added TMOF (90 vol) and the mixture heated to a temperature of 105° C. for 3 hours under $N_2$. The TMOF was concentrated under reduced pressure to give a crude orange coloured solid. The crude solid was triturated in TMBE (4 vol), filtered, washed with TMBE (1×3 vol) and dried to give 5-methoxymethylene-2,2-dimethyl-[1,3]dioxane-4,6-dione.

Step 3

To a stirred solution of the 1-(3,4-dichloro-phenyl)-ethanone oxime (1 eq) in dry THF (6 vol) cooled externally to −15° C. was added 2.5M n-BuLi (2.2 eq) dropwise. After stirring the reaction mixture for 75 minutes, 5-methoxymethylene-2,2-dimethyl-[1,3]dioxane-4,6-dione (1.0 eq) in THF (9 vol) was added to the externally cooled reaction mixture. After 1 hour the reaction mixture was warmed to 0° C. for 15 minutes, and then stirred for 16 hours at room temperature. The reaction mixture was added to water (27 vol) and extracted with TBME (2×7 vol). The aqueous layer was acidified with 5M $H_2SO_4$ (3 vol) and further extracted with TMBE (3×7 vol). The combined organics were filtered and concentrated under reduced pressure to give a crude residue.

Step 4

Water (1 vol) was added to the crude residue from step 2, dissolved in DMF (6 vol) and the mixture was heated at a temperature of 110° C. for 45 minutes. The cooled reaction mixture was added to water (27 vol) and extracted with a mixture of TBME (7 vol) and EtOAc (7 vol) after saturated aqueous NaCl solution (14 vol) was added. The aqueous layer was further extracted with EtOAc (2×7 vol). The combined organics were washed with water (3×27 vol), a 1:1 mixture of saturated aqueous NaCl solution (55 vol) and water (55 vol), dried over $MgSO_4$ and concentrated under reduced pressure to give a crude residue. This was partially purified by dry flash column chromatography (eluent: [98:2] DCM:MeOH). The solid obtained was dissolved in saturated sodium bicarbonate solution (40 vol), washed with TBME (14 vol) and heptane (14 vol). The basic aqueous solution was passed through a glass frit and the pH was adjusted to 1 using $5NH_2SO_4$ (11 vol) before being extracted with EtOAc (2×34 vol). The combined organics were washed with a (1:1) mixture of saturated aqueous NaCl solution (14 vol) and water (1×14 vol), dried over $MgSO_4$ and concentrated under reduced pressure. The solid was further purified by trituration in TMBE (1.5 vol), filtered and washed with TBME (1.5 vol) to yield [3-(3,4-Dichloro-phenyl)-4,5-dihydro-isoxazol-5-yl]-acetic acid.

Step 5

Acetyl chloride (5 eq) was added to MeOH (50 vol) externally cooled with a mixture saturated aqueous NaCl solution and ice. After 10 minutes the solution was warmed to room temperature. After a further 90 minutes, [3-(3,4-dichloro-phenyl)-4,5-dihydro-isoxazol-5-yl]-acetic acid (1.0 eq) in MeOH (25 vol) was added to the hydrogen chloride methanolic solution and stirred for 16 hours. The solvent was concentrated under reduced pressure and the residue was purified by flash column chromatography (eluent: [3:7] EtOAc:heptane) to afford [3-(3,4-dichloro-phenyl)-4,5-dihydro-isoxazol-5-yl]-acetic acid methyl ester.

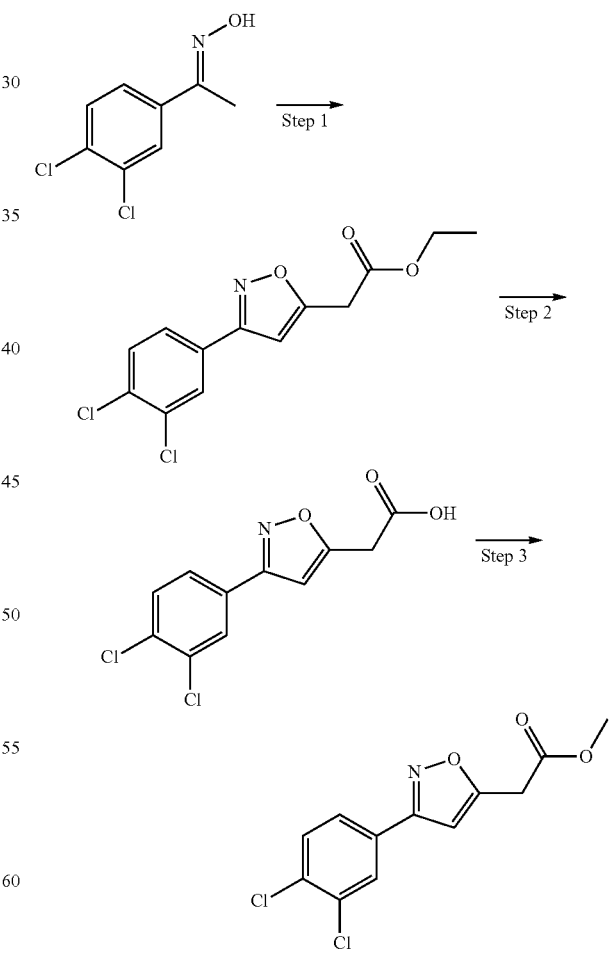

| Structure | Molecular Weight | Mass Spec Result |
|---|---|---|
| 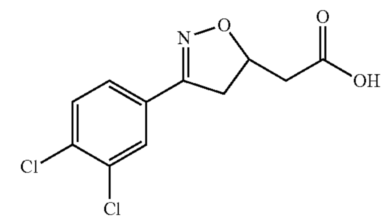 [SMILES: O=C(O)CC1CC(c2ccc(Cl)c(Cl)c2)=NO1] | 274.11 | $[M + H]^+$ = 274, 99% @ rt = 3.73 min |
| 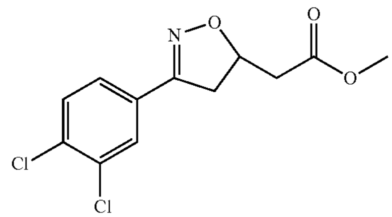 [SMILES: COC(=O)CC1CC(c2ccc(Cl)c(Cl)c2)=NO1] | 288.13 | $[M + H]^+$ = 288, 93% @ rt = 4.21 min |

Example 4

Preparation of 3,5-isoxazoles

Step 1

To a solution of ethyl 2,3-butadienoate (1 eq) and 1-(3,4-dichloro-phenyl)-ethanone oxime (1.03 eq) in DCM (51 vol) was added a 10% aqueous bleach solution (51 vol) and the resultant biphasic system stirred at room temperature for 5 days. The organic layer was separated and the aqueous layer extracted with DCM (3×7 vol). The combined organic layers were washed with water (36 vol), dried over MgSO₄, filtered and concentrated. The crude residue was purified by a combination of flash column chromatography (eluent: [0:1 to 1:2] EtOAc:heptane) and prep HPLC to yield [3-(3,4-Dichloro-phenyl)-isoxazol-5-yl]-acetic acid ethyl ester.

Step 2

To a solution of the Step 1 ester (1 eq) in EtOH (50 vol) was added an aqueous solution of NaOH (2M, 5 eq) and the mixture stirred at room temperature. After 10 minutes further EtOH (50 vol) was added to aid solubility and then stirred for 48 hours. The reaction mixture was concentrated in vacuo and water (125 vol) added to the residue. An aqueous solution of HCl (2M, 25 vol) was added and a white solid precipitated out. The precipitated solid was filtered, washed with water (2×10 vol) and dried to give [3-(3,4-Dichloro-phenyl)-isoxazol-5-yl]-acetic acid.

Step 3

To a stirred solution of the Step 2 acid (1 eq) in DCM (100 vol) was added thionyl chloride (50 vol) under an atmosphere of nitrogen gas at room temperature. Further amounts of thionyl chloride (50 and 20 vol respectively) were added in stages until the reaction was completed after 4 hours. The solvent was concentrated; DCM (100 vol) and then MeOH (50 vol) were added and the solution was stirred for 1 hour. Water was then added and a precipitate had formed. The organics were concentrated and dried to yield [3-(3,4-Dichloro-phenyl)-isoxazol-5-yl]-acetic acid methyl ester.

| Structure | Molecular Weight | Mass Spec. Result |
|---|---|---|
| [structure] | 300.14 | [M + H]⁺ = 301, 100% @ rt = 4.83 min |
| [structure] | 272.09 | [M + H]⁺ = 272, 100% @ rt = 4.03 min |
| [structure] | 286.12 | [M + H]⁺ = 286/288, 100% @ rt = 4.48 min |

Example 5

Preparation of 3,5-isoxazoles

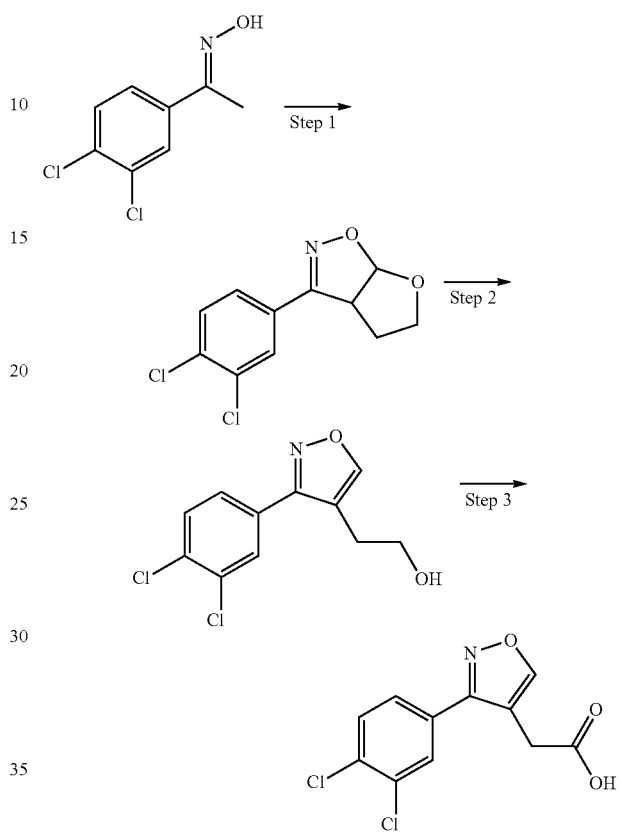

Step 1

To a suspension of 3,4-dichlorobenzaldehyde oxime (1 eq) in DCM (10 vol) was added a 50% aqueous bleach solution (10 vol). 2,3-Dihydrofuran was then added and the resultant biphasic system was stirred vigorously at room temperature for 21 hours. Water (25 vol) and brine (25 vol) were added and the organic layer was separated. The aqueous phase was further extracted with (2×5 vol) DCM. The combined organic phases were washed with a 1:1 mixture of water and brine (50 vol), dried over MgSO₄, filtered and concentrated. The crude residue was purified by flash column chromatography (eluent: EtOAc:heptane) to yield 3-(3,4-Dichloro-phenyl)-3a,4,5,6a-tetrahydro-furo[3,2-d]isoxazole.

Step 2

To the Step 1 tetrahydro-furo[3,2-d]isoxazole in 80% EtOH (5.8 vol) was added concentrated HCl (0.7 wt) and heated to 90° C. for 27 hours. The organic solvent was concentrated. A 1:1 mixture of water and brine (29 vol) was added and the organics extracted with (3×7 vol) DCM. The combined organic phases were washed with brine (14 vol), dried over MgSO₄, filtered and concentrated. The crude residue was purified by flash column chromatography (eluent: EtOAc:heptane) to yield 2-[3-(3,4-Dichloro-phenyl)-isoxazol-4-yl]-ethanol.

Step 3

To a partially cooled solution of the Step 2 alcohol in acetic acid (10 vol) was added drop wise a solution of CrO₃ (1.3 eqv) in 80% acetic acid (10 vol). After 5 minutes the reaction mixture was then stirred at room temperature for 1 day. A further amount of CrO$_3$ (1.3 eqv) in water (2 vol) was added at room temperature and the reaction stirred for another 2 hours. The acetic acid was concentrated and then a mixture of water and brine (113 vol) and EtOAc (50 vol) were added. The organic layer was separated and the aqueous layer was further extracted with EtOAc (3×25 vol). The combined organic phases were washed with a 1:2 mixture of water and brine (75 vol), dried over MgSO$_4$, filtered and concentrated. The crude residue was extracted with 2N NaOH (13 vol) and washed with TBME (50 vol). The biphasic system was filtered and the organic phase extracted with a further amount of 2N NaOH (13 vol). The combined aqueous phases were washed with TBME (13 vol), acidified with concentrated HCl and extracted with EtOAc (2×26 vol; 1×13 vol). The combined organic phases were washed with brine (26 vol), dried over MgSO$_4$, filtered and concentrated. The crude residue was purified by flash column chromatography (eluent: MeOH:DCM) and prep HPLC to yield [3-(3,4-Dichloro-phenyl)-isoxazol-4-yl]-acetic acid.

| Structure | Molecular Weight | Mass Spec. Result |
|---|---|---|
| 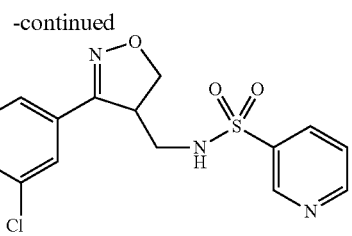 | 272.09 | [M + H]+ = 272/274, 98% @ rt = 3.92 min |

Example 6

Preparation of 3,4-isoxazoline analogues

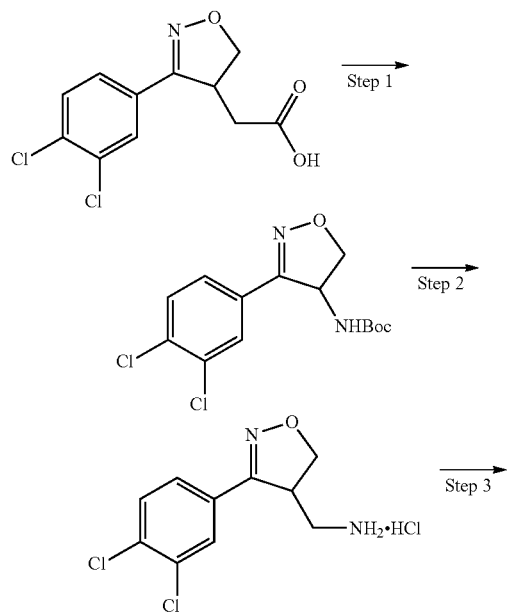

Step 1

[3-(3,4-Dichloro-phenyl)-4,5-dihydro-isoxazol-4-yl]-acetic acid (1 eq) was added to warm tert-butanol (10 vol) at 30° C. Triethylamine (1 eq) was then added and the mixture stirred for 5 minutes. DPPA (1 eq) was then added and the mixture was heated to 80° C. for 1 day. The tert-butanol was concentrated, water (20 vol) was added and the organics extracted with EtOAc (15 vol). The organic phase was washed with a mixture of acidified (2N citric acid) water & brine (>10 vol), a mixture of saturated NaHCO$_3$ and brine (10 vol), dried over MgSO$_4$, filtered and concentrated. The crude residue was purified by flash column chromatography (eluent: EtOAc:heptane) to yield [3-(3,4-Dichloro-phenyl)-4,5-dihydro-isoxazol-4-ylmethyl]-carbamic acid tert-butyl ester.

Step 2

The Step 1 protected amine (1 eq) was added to a solution of HCl in MeOH (25 vol) (generated from acetyl chloride (5 eq) in MeOH) and stirred at room temperature for 21 hours. A further amount of HCl in MeOH (3.5 vol) (generated from acetyl chloride (3.4 eq) in MeOH) was then added and the solution stirred for another 3.5 hours. The organic solvent was concentrated, the residue was triturated with TBME (7 vol), filtered, washed with more TBME (2×4 vol) and dried to yield C—[3-(3,4-Dichloro-phenyl)-4,5-dihydro-isoxazol-4-yl]-methylamine hydrochloride salt.

Step 3

To a mixture of the Step 2 salt (1 eq) and pyridine-3-sulfonyl chloride (1.5 eq) was added pyridine (5 vol) and the reaction stirred at room temperature for 2 hours. Water was then added and the organics extracted with EtOAc (300 vol). The organic phase was then washed with water (3×250 vol), brine (2×125 vol), dried over MgSO$_4$, filtered and concentrated to yield crude Pyridine-3-sulfonic acid [3-(3,4-dichloro-phenyl)-4,5-dihydro-isoxazol-4-ylmethyl]-amide.

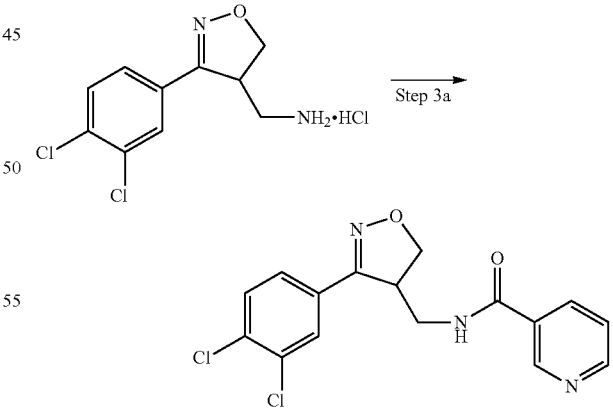

Step 3a

To a stirred solution of nicotinic acid (1 eq) in DMF (13 vol) was added HOBt (1.2 eq) and EDC.HCl (1.2 eq) at room temperature. To this mixture was added the free-based (using triethylamine (1.1 eq)) salt of C-[3-(3,4-dichloro-phenyl)-4,5-dihydro-isoxazol-4-yl]-methylamine hydrochloride (1 eq) in DMF (10 vol) and the reaction was stirred at room temperature for 18 hours. Water (100 vol) was added and the pH adjusted to 12 using 2N NaOH. The oily precipitation was extracted with EtOAc (2×67 vol). The organic phases were combined and washed with water (3×67 vol), brine (1×67 vol), dried over MgSO₄, filtered and concentrated. The crude residue was purified by flash column chromatography (eluent: EtOAc:heptane) to yield N-[3-(3,4-Dichloro-phenyl)-4,5-dihydro-isoxazol-4-ylmethyl]-nicotinamide.

| Structure | Molecular Weight | Mass Spec. Result |
|---|---|---|
| (isoxazoline with 3,4-dichlorophenyl and sulfonamide-pyridine) | 386.26 | [M + H]+ = 386/388, 100% @ rt = 3.91 min |
| (isoxazoline with 3,4-dichlorophenyl and amide-pyridine) | 350.21 | [M + H]+ = 350/352, 100% @ rt = 3.63 min |

Example 7

Preparation of 3,4-isoxazoline analogues

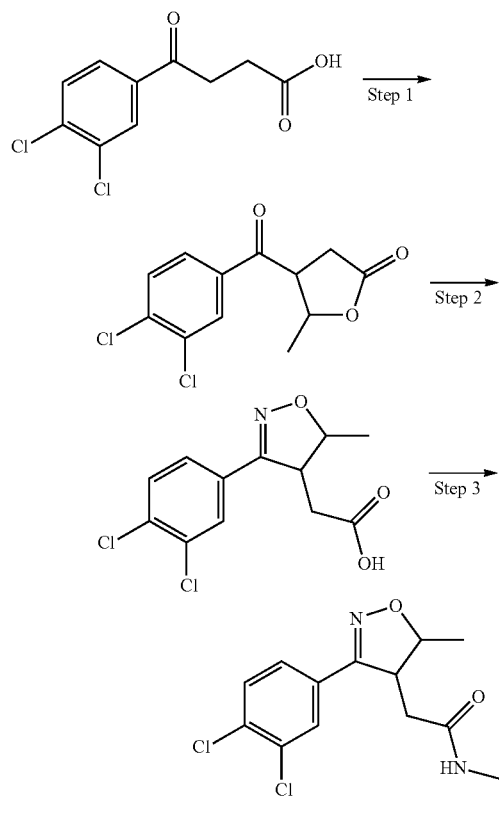

Step 1

To a suspension of the ketoacid (1 eq) in water (20 vol) was added K₂CO₃ (0.73 eq) at room temperature. On completed dissolution, acetaldehyde (1.1 eq) was added and the reaction mixture was stirred for 18 days at room temperature. Concentrated HCl (6 vol) was added and the reaction mixture heated to 100° C. for 2 hours and then cooled. The organics were extracted with DCM (2×40 vol). The organic phase was then washed with saturated NaHCO₃, brine, dried over MgSO₄, filtered and concentrated to yield 4-(3,4-Dichlorobenzoyl)-5-methyl-dihydro-furan-2-one.

Step 2

To a solution of the Step 1 product (1 eq) in ethanol (5 vol) and water (5 vol) was added hydroxylamine hydrochloride (1.48 eq) and ammonium acetate (1.48 eqv). The reaction mixture was heated to 90° C. for 4 hours and then cooled. The solvent was concentrated; saturated NaHCO₃ was added and washed with EtOAc. The aqueous phase was acidified to pH 1 using concentrated HCl. On standing for 1.5 days, the resultant precipitate was filtered to yield [3-(3,4-Dichlorophenyl)-5-methyl-4,5-dihydro-isoxazol-4-yl]-acetic acid.

Step 3

To a mixture of the Step 2 acid (1 eq), EDC.HCl (1.2 eq) and HOBt (1.2 eq) in DMF (33 vol) were stirred at room temperature for 1 day. The reaction mixture was then heated to 60° C. for 6 hours and then cooled. Water was then added and the organics extracted with DCM. The organic phase was washed with saturated NaHCO₃, dried over Na₂SO₄, filtered and concentrated. The crude residue was purified by flash column chromatography (eluent: EtOAc:heptane) to yield 2-[3-(3,4-Dichloro-phenyl)-5-methyl-4,5-dihydro-isoxazol-4-yl]-N-pyrimidin-5-yl-acetamide.

| Structure | Molecular Weight | Mass Spec. Result |
|---|---|---|
| (isoxazoline with 3,4-dichlorophenyl, methyl and acetic acid) | 288.13 | [M + H]+ = 288/290, 97% @ rt = 4.16 min |
| (isoxazoline with 3,4-dichlorophenyl, methyl and pyrimidinyl amide) | 365.22 | [M + H]+ = 365/367, 93% @ rt = 4.23 min |

Example 8

Preparation of 3,4-isoxazoline analogues

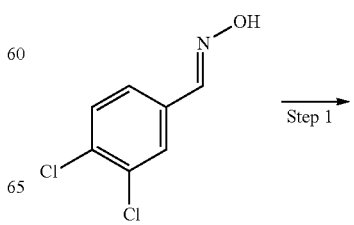

-continued

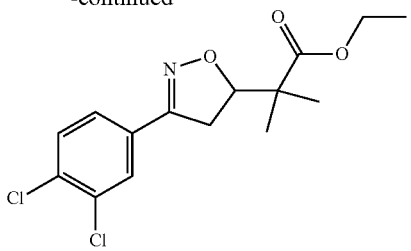

To a solution of the aldoxime (prepared from Example 1) (1 eq) in DCM (40 vol) was added 10% bleach solution (40 vol) and then 2,2-dimethyl-but-3-enoic acid ethyl ester (3.4 eq). The biphasic system was stirred vigorously for 2 hours at room temperature. The organic phase was separated and washed with water, dried, filtered and concentrated. The crude residue was purified by flash column chromatography (eluent: EtOAc:heptane) to yield 2-[3-(3,4-Dichloro-phenyl)-4,5-dihydro-isoxazol-5-yl]-2-methyl-propionic acid ethyl ester.

| Structure | Molecular Weight | Mass Spec. Result |
|---|---|---|
| 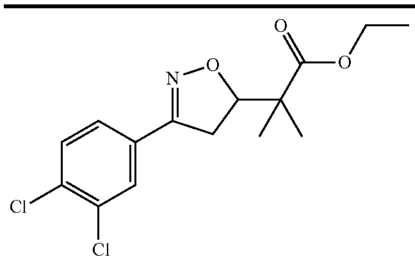 | 330.21 | [M + H]+ = 330/332, 91% @ rt = 4.96 min |

Example 9

Following similar procedures to those described above, the following compound was prepared.

| Structure | Molecular Weight | Mass Spec. Result |
|---|---|---|
| 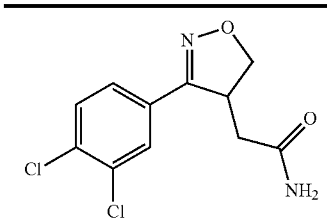 | 273.12 | [M + H]+ = 273/275, 99% @ rt = 3.56 min |

Example 10

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 µl in 96 well cell plate
Substrate: L-Kynurenine (Sigma: Cat# K3750, stock concentration: 10 mM in 100 mM potassium phosphate buffer, pH 7.4)
Assay Conditions:
Medium: OptiMem (Reduced Serum Medium 1×, +L-Glutamine+HEPES—Phenol Red; GIBCO: Cat#11058)
Assay Volume: 200 µl
Plate Format: 96 well plate, transparent (Corning)
Read-Out: product (3OH-KYN) quantification using product specific MRM
Reader: LC/MS/MS
Assay Protocol:
  prepare serial dilution (factor 3) of compound in 100% DMSO (top concentration=6.67 mM, 100% DMSO)
  [8 points: 6.67 mM; 2.22 mM; 0.74 mM; 0.247 mM; 0.082 mM; 0.027 mM; 0.009 mM; 0.003 mM]
  prepare 300-fold concentrated solution of each compound concentration (top concentration 22.22 µM, 0.3% DMSO) in OptiMem medium
  [22.2 µM; 7.41 µM; 2.47 µM; 0.82 µM; 0.27 µM; 0.09 µM; 0.03 µM; 0.01 µM]
  prepare substrate (10 mM) at concentration of 1.1 mM in medium
  medium of cell plate is drawed off
  cells are washed with OptiMem (100 µl/well) and drawed off again
  assay mix: 90 µl OptiMem/well+90 µl compound/well of each concentration
  [final compound top concentration: 10 µM; 0.15% DMSO]
  [final compound bottom concentration: 0.004 µM; 0.15% DMSO]
  pre-incubation: 30 min at 37° C.
  add 20 µl/well of the 1.1 mM substrate solution (final assay concentration: 100 µM)
  positive control: 200 µl OptiMem
  negative control: 180 µl OptiMem+20 µl 1.1 mM substrate incubate ~24 h at 37° C.
  transfer 100 µl of each well in a transparent 96 well plate (Corning)
  add 100 µl/well 10% trichloro acetic acid (TCA) in water
  centrifugate plate for 3 min at 4000 rpm
  detect product by LC/MS (injection of 50 µl/well; 2.5 fold overfill of the 20 µl sample loop)
Data Analysis:
  $IC_{50}$'s are calculated using automated fitting algorithm (A+Analysis).

Example 11

A method of monitoring L-Kynurenine (KYN) hydroxylation to form product 3-Hydroxy-Kynurenine (3OH-KYN) by LC/MS is described below. Product is quantified by multiple reaction monitoring.
Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat# K3750)
  [stock concentration: 10 mM in 100 mM potassium phosphate buffer, pH 7.4]
Assay Conditions:
Buffer: 100 mM potassium phosphate, pH 7.4, 200 µM NADPH, 0.4 U/ml G6P-DH (Glucose 6-phosphate dehydrogenase), 3 mM G6P (D-Glucose 6-phosphate)
Assay Volume: 40 µl
Plate Format: 384 well plate, transparent (Matrix)

Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
  [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
  [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO human enzyme+4 µl 1 mM substrate (final concentration=100 µM)
  [final compound top concentration: 30 µM; 0.3% DMSO]
  [final compound bottom concentration: 0.0137 µM; 0.3% DMSO]
  positive control: 4 µl 50 µM FCE28833 in assay buffer [0.5% DMSO] (final assay concentration=5 µM)+24 µl assay buffer/well+8 µl KMO human enzyme+4 µl 1 mM substrate (final concentration=100 µM)
  negative control: 28 µl assay buffer/well+8 µl KMO human enzyme+4 µl 1 mM substrate (final concentration=100 µM)
  incubate 400 min at RT
  add 40 µl/well 10% trichloro acetic acid in water to stop the assay and precipitate protein
  centrifuge plate for 3 min at 4000 rpm
  product detection by LC/MS (injection of 50 µl/well; 2.5 fold overfill of the 20 µl sample loop)
Data Analysis:
  $IC_{50}$'s are calculated using automated fitting algorithm (A+Analysis).

Example 12

A method of monitoring L-Kynurenine (KYN) hydroxylation to form 3-Hydroxy-Kynurenine (3OH-KYN) by LC/MS is described. Product is quantified by multiple reaction monitoring (MRM method).
Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration: 10 mM in 100 mM potassium phosphate buffer, pH 7.4)
Assay Conditions:
Buffer: 100 mM potassium phosphate, pH 7.4, 200 µM NADPH, 0.4 U/ml G6P-DH (Glucose 6-phosphate Dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
  [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
  [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assaybuffer/well+8 µl KMO mouse enzyme+4 µl 1 mM substrate (final concentration=100 µM)
  [final compound top concentration: 30 µM; 0.3% DMSO]
  [final compound bottom concentration: 0.0137 µM; 0.3% DMSO]
  positive control: 4 µl 50 µM FCE28833 in assay buffer, 0.5% DMSO [final assay concentration=5 µM]+24 µl assaybuffer/well+8 µl KMO mouse enzyme+4 µl 1 mM substrate [final concentration=100 µM]
  negative control: 28 µl assay buffer/well+8 µl KMO mouse enzyme+4 µl 1 mM substrate [final concentration=100 µM]
  incubate 40 min at RT
  add 40 µl/well 10% trichloro acetic acid in water to stop the assay and precipitate protein
  centrifuge plate for 3 min at 4000 rpm
  product detection by LC/MS (injection of 20 µl/well, 2 fold overfill of the 10 µl sample loop)
Data Analysis:
  $IC_{50}$'s are calculated using automated fitting algorithm (A+Analysis).

Example 13

Using procedures similar to those described herein, the following compounds were assayed for activity.

| IUPAC name | INH.Mouse @ 10 µM |
| --- | --- |
| [3-(3,4-Dichloro-phenyl)-4,5-dihydro-isoxazol-4-yl]-acetic acid methyl ester | 102.45 |
| [3-(3,4-Dichloro-phenyl)-4,5-dihydro-isoxazol-4-yl]-acetic acid | 101.21 |
| 3-(3-Chloro-phenyl)-4,5-dihydro-isoxazol-4-yl]-acetic acid | 105.65 |
| [3-(3,4-Dichloro-phenyl)-4,5-dihydro-isoxazol-5-yl]-acetic acid | 93.35 |
| [3-(3,4-Dichloro-phenyl)-4,5-dihydro-isoxazol-5-yl]-acetic acid methyl ester | 88.41 |
| 2-[3-(3,4-Dichloro-phenyl)-4,5-dihydro-isoxazol-4-yl]-N-pyridin-3-yl-acetamide | 77.23 |

| IUPAC name | INH.Mouse @ 10 µM |
|---|---|
| 2-[3-(3,4-Dichloro-phenyl)-4,5-dihydro-isoxazol-4-yl]-N-(2-methyl-pyrimidin-5-yl)-acetamide | 81.17 |
| 2-[3-(3,4-Dichloro-phenyl)-4,5-dihydro-isoxazol-4-yl]-N-pyrimidin-5-yl-acetamide | 82.65 |
| [3-(3,4-Dichloro-phenyl)-isoxazol-5-yl]-acetic acid ethyl ester | 60.84 |
| [3-(3,4-Dichloro-phenyl)-isoxazol-5-yl]-acetic acid | 74.53 |
| [3-(3,4-Dichloro-phenyl)-isoxazol-5-yl]-acetic acid methyl ester | 66.4 |
| [3-(3,4-Dichloro-phenyl)-isoxazol-4-yl]-acetic acid | 74.7 |
| 2-[3-(3,4-Dichloro-phenyl)-4,5-dihydro-isoxazol-4-yl]-acetamide | 60.4 |
| [3-(3,4-Dichloro-phenyl)-5-methyl-4,5-dihydro-isoxazol-4-yl]-acetic acid | 84.5 |
| 2-[3-(3,4-Dichloro-phenyl)-4,5-dihydro-isoxazol-4-yl]-N-(3-methyl-isoxazol-5-yl)-acetamide | 64 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. At least one chemical entity chosen from compounds of Formula VI

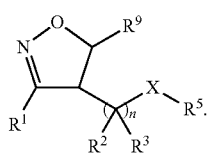

Formula VI and pharmaceutically acceptable salts and prodrugs thereof wherein:

$R^1$ is chosen from aryl and heteroaryl, each of which is substituted with one, two, or three groups chosen from halo, lower alkyl, lower alkoxy, optionally substituted amino, optionally substituted heterocycloalkyl, optionally substituted heteroaryl, and hydroxy;

$R^2$ and $R^3$ are independently chosen from hydrogen and lower alkyl;

$R^5$ is chosen from hydrogen, optionally substituted alkyl, optionally substituted cycloalkyl, optionally substituted heterocycloalkyl, optionally substituted aryl, and optionally substituted heteroaryl;

n is chosen from 1 and 2; and

X is —C(O)O—;

$R^9$ is chosen from hydrogen and lower alkyl provided that —$R^1$ is not 4-hydroxyphenyl.

2. At least one chemical entity of claim 1 wherein the compound of Formula VI is chosen from compounds of Formula III

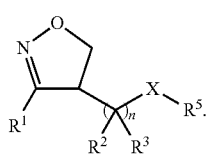

Formula III

3. At least one chemical entity of claim 1 wherein n is one.

4. At least one chemical entity of claim 1 wherein for each occurrence, at least one of $R^2$ and $R^3$ is hydrogen.

5. At least one chemical entity of claim 4 wherein for each occurrence, $R^2$ and $R^3$ are hydrogen.

6. At least one chemical entity of claim 1 wherein $R^5$ is chosen from hydrogen and lower alkyl.

7. At least one chemical entity of claim 6 wherein $R^5$ is chosen from hydrogen, methyl, and ethyl.

8. At least one chemical entity of claim 1 wherein $R^1$ is chosen from optionally substituted phenyl and optionally substituted heteroaryl.

9. At least one chemical entity of claim 8 wherein $R^1$ is chosen from pyridinyl and phenyl optionally substituted with one, two or three halo groups.

10. At least one chemical entity of claim 9 wherein $R^1$ is phenyl optionally substituted with one or two halo groups.

11. At least one chemical entity of claim 10 wherein $R^1$ is 3,4-dihalophenyl.

12. At least one chemical entity of claim 11 wherein $R^1$ is 3,4-dichlorophenyl.

13. At least one chemical entity of claim 1 wherein the compound of formula I is chosen from
[3-(3,4-Dichloro-phenyl)-4,5-dihydro-isoxazol-4-yl]-acetic acid;
[3-(3-Chloro-phenyl)-4,5-dihydro-isoxazol-4-yl]-acetic acid; and
[3-(3,4-Dichloro-phenyl)-5-methyl-4,5-dihydro-isoxazol-4-yl]-acetic acid.

14. A pharmaceutical composition comprising at least one chemical entity of claim 1 and at least one pharmaceutically acceptable excipient.

15. A method of treating a condition or disorder mediated by Kynurenine 3-mono-oxygenase activity in a subject in need of such a treatment which method comprises administering to the subject a therapeutically effective amount of at least one chemical entity of claim 1.

16. The method of claim 15 wherein at least one chemical entity binds Kynurenine 3-mono-oxygenase.

17. The method of claim 15 wherein said condition or disorder involves a neurodegenerative pathology.

18. The method of claim 17 wherein the neurodegenerative pathology is selected from Huntington's disease, Alzheimer's disease, Parkinson's disease, olivoponto cerebellar atrophy, non-Alzheimer's dementia, multi-infarctual dementia, cerebral amyotrophic lateral sclerosis, cerebral ischemia, cerebral hypoxia, spinal or head trauma and epilepsy.

19. A packaged pharmaceutical composition comprising at least one pharmaceutical composition of claim 14 and instructions for using the composition to treat a subject suffering from a condition or disorder mediated by Kynurenine 3-mono-oxygenase activity.

20. The packaged pharmaceutical composition of claim 19, wherein the condition or disorder is Huntington's disease.

* * * * *